(12) United States Patent
Lappi et al.

(10) Patent No.: US 7,741,435 B2
(45) Date of Patent: *Jun. 22, 2010

(54) SUBSTANCE P-SAPORIN (SP-SAP) CONJUGATES AND METHODS OF USE THEREOF

(75) Inventors: Douglas A. Lappi, Del Mar, CA (US); Ronald G. Wiley, Brentwood, TN (US)

(73) Assignee: Advanced Targeting Systems, Inc., San Diego, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 10/813,856

(22) Filed: Mar. 30, 2004

(65) Prior Publication Data

US 2004/0253248 A1 Dec. 16, 2004

Related U.S. Application Data

(63) Continuation of application No. 09/523,790, filed on Mar. 13, 2000, now abandoned, which is a continuation-in-part of application No. 08/890,157, filed on Jul. 9, 1997, now Pat. No. 6,063,758.

(51) Int. Cl.
*A61K 38/00* (2006.01)
*A61K 47/48* (2006.01)
*C07K 14/415* (2006.01)
*C07K 7/00* (2006.01)

(52) U.S. Cl. .................. 530/326; 530/350; 514/13; 514/12; 514/2

(58) Field of Classification Search .................. None
See application file for complete search history.

(56) References Cited

U.S. PATENT DOCUMENTS

| 5,191,067 | A | | 3/1993 | Lappi et al. |
| 5,679,637 | A | | 10/1997 | Lappi et al. |
| 6,063,758 | A | * | 5/2000 | Lappi et al. .................. 514/2 |

FOREIGN PATENT DOCUMENTS

WO 97/13410 * 4/1997

OTHER PUBLICATIONS

Abbadie et al., "Inflammation increases the distribution of dorsal horn neurons that internalize the neurokinin-1 receptor in response to noxious and non-noxious stimulation," *J. Neurosci.* 17:8049-8060 (1997).
Anderson et al., "Dopamine $D_1$ receptor-stimulated release of acetylcholine in rat striatum is mediated indirectly by activation of striatal neurokinin$_1$ receptors," *J. Pharmacol. Exp. Therap.* 269:1144-1151 (1994).
Anton et al., "Development of a biotinylated analog of substance P for use as a receptor probe," *Laboratory Investigation* 64:703-708 (1991).
Boehmer et al,. "High levels of mRNA coding for substance P, somatostatin and alpha-tubulin are expressed by rat and rabbit dorsal root ganglia neurons," *Peptides* 10:1179-1194 (1989).
Bozic et al., "Neurogenic amplification of immune complex inflammation," *Science* 273:1722-1725 (1996).
Brelje et al., "Three-dimensional imaging of intact isolated islets of Langerhans with confocal microscopy," *Diabetes* 38:808-814 (1989).
Brimijoin et al., "Axonal transport of substance P in the vagus and sciatic nerves of the guinea pig," *Brain Research* 191:443-457 (1980).
Brown et al., "Morphological characterization of substance P receptor-immunoreactive neurons in the rat spinal cord and trigeminal nucleus caudalis," *J. Comp. Neurol.* 356:327-344 (1995).
Buechler et al., "Synthesis and characterization of a homogeneous chemical conjugate between basic fibroblast growth factor and saporin." *Eur. J. Biochem.* 234(3):706-713 (1995).
Chapman and Dickenson, "The effect of intrathecal administration of RP67580, a potent neurokinin 1 antagonist on nociceptive transmission in the rat spinal cord," *Neurosci. Lett.* 157:149-152 (1993).
De Konick et al., "Substance P-mediated slow excitatory postsynaptic potential elicited in dorsal horn neurons in vivo by noxious stimulation," *Proc. Natl. Acad. Sci. USA* 88:11344-11348 (1991).
Del Fiacco et al., "GAP-43 persists in adulthood and coexists with SP and CGRP in human trigeminal sensory neurons," *NeuroReport* 5:2349-2352 (1994).
Ding, et al., "Spinoparabrachial tract neurons showing substance P receptor-like immunoreactivity in the lumbar spinal cord of the rat," *Brain Research* 674:336-340 (1995).
Dougherty et al., "Combined application of excitatory amino acids and substance P produced long-lasting changes in responses of primate spinothalamic tract neurons," *Brain Res. Rev.* 18:227-246 (1993).

(Continued)

*Primary Examiner*—Michael Borin
(74) *Attorney, Agent, or Firm*—McDermott Will & Emery LLP

(57) ABSTRACT

This invention provides a conjugate comprising Substance P, or an analog thereof, and a protein, such as Saporin, that inhibits protein synthesis.

This invention provides a method of reducing the perception of pain by a subject comprising administering to the subject an effective amount of the pharmaceutical composition of the conjugate comprising Substance P, or an analog thereof, and a protein such as Saporin that inhibits protein synthesis, so as to reduce the perception of pain by the subject.

This invention provides a method of selectively destroying NK-1R-expressing neuronal cells in a subject comprising administering to the subject an effective amount of the conjugate comprising Substance P, or an analog thereof, and a protein such as Saporin that inhibits protein synthesis, so as to selectively destroy NK-1R-expressing neuronal cells.

Lastly, this invention provides a method for treating a NK-1R-associated disorder in a subject, which comprises administering to the subject an amount of the pharmaceutical composition comprising substance P, or an analog thereof, and a protein such as Saporin that inhibits protein synthesis, in an effective amount to treat the disorder associated with the NK-1R.

16 Claims, 12 Drawing Sheets

OTHER PUBLICATIONS

Dougherty et al., "Enhancement of spinothalamic neuron responses to chemical and mechanical stimuli following combined micro-iontophoretic application of N-methyl-D-aspartic acid and substance P," *Pain* 47:85-93 (1991).

Duggan et al., "Sustained isometric contraction of skeletal muscle results in release of immunoreactive neurokinins in the spinal cord of the anaesthetized cat," *Neurosci. Lett.* 122:191-194 (1991).

Gilchrist et al., "Enhanced withdrawal responses to heat and mechanical stimuli following intraplantar injection of capsaicin in rats," *Pain* 67:179-188 (1996).

Grady et al., "Delineation of the endocytotic pathway of substance P and its seven-transmembrane domain NK1 receptor," *Mol. Biol. Cell* 6:509-524 (1995).

Guzman et al., "Effect of substance P on acetylcholine and dopamine release in the rat striatum: a microdialysis study," *Brain Research* 622:147-154 (1993).

Hargreaves et al., "A new and sensitive method for measuring thermal nociception in cutaneous hyperalgesia," *Pain* 32:77-88 (1988).

Hokfelt et al., "Experimental immunohistochemical studies on the localization and distribution of substance P in cat primary sensory neurons," *Brain Research* 100:235-252 (1975).

Humpel, "Intranigral injection of selective neurokinin-1 and neurokinin-3 but not neurokinin-2 receptor agonists biphasically modulate striatal dopamine metabolism but not striatal preprotachykinin-A mRNA in the rat," *Neurosci. Lett.* 157:223-226 (1993).

Jessell and Iversen, "Opiate analgesics inhibit substance P release from rat trigeminal nucleus," *Nature* 268:549-551 (1977).

Kar et al., "Altered calcitonin gene-related peptide, substance P and enkephalin immunoreactivities and receptor binding sites in the dorsal spinal cord of the polyarthritic rat," *Eur J. Neurosci.* 6:345-354 (1994).

Kim and Chung, "An experimental model for peripheral neuropathy produced by segmental spinal nerve ligation in the rat," *Pain* 50:355-363 (1992).

Lambert et al., "Purified immunotoxins that are reactive with human lymphoid cells," *J. Biol. Chem.* 260:12035-12041 (1985).

Lappi et al., "Biological and chemical Characterization of basic FGF-saporin mitotoxin." *Biochem. Biophys. Res Commun.* 160(2):917-923 (1989).

Lappi et al., "Characterization of a *Saponaria officinalis* seed ribosome-inactivating protein: immunoreactivity and sequence homologies." *Biochem. Biophys. Res. Commun.* 129(3):934-942 (1985).

Lappi et al., "Characterization of a saporin mitotoxin specifically cytotoxic to cells bearing the granulocyte-macrophage colony-stimulating factor." *Growth Factors* 9(1):31-39 (1993).

Lappi et al., "Reducing the heterogenecity of chemically conjugated targeted toxins: homogeneous basic FGF-saporin," *Analytical Biochemistry*, 212(2):446-451 (1993).

Littlewood, et al., "The types of neuron in spinal dorsal horn which possess neurokinin-1 receptors," *Neuroscience* 66:597-608 (1995).

Liu et al,. "Synaptic relationship between substance P and the substance P receptor: light and electron microscopic characterization of the mismatch between neuropeptides and their receptors," *Proc. Natl. Acad. Sci. USA* 91:1009-1013 (1994).

Luo and Wisenfeld-Hallim, "The effects of pretreatment with tachykinin antagonists and galanin on the development of spinal cord hyperexcitability following sciatic nerve section in the rat," *Neuropeptides* 28:161-166 (1995).

Ma et al., "Involvement of neurokinin receptors in the induction but not the maintenance of mechanical allodynia in rat flexor motoneurones," *J. Physiol.* (London) 486:769-777.

Malmberg et al., "Hyperalgesia mediated by spinal glutamate or substance P receptor blocked by spinal cyclooxygenase inhibition," *Science* 257:1276-1279 (1992).

Mantyh et al., "Beta 2-adrenergic receptors are expressed by glia in vivo in the normal and injured central nervous system in the rat, rabbit, and human," *J. Neurosci.* 15:152-164 (1995).

Mantyh et al., "Some sensory neurons express neuropeptide Y receptors: potential paracrine inhibition of primary afferent nociceptors following peripheral nerve injury," *J. Neurosci.* 14:3958-3968 (1994).

Mantyh, et al., "Receptor endocytosis and dendrite reshaping in spinal neurons after somatosensory stimulation," *Science* 268-1629-1632 (1995).

Marshall et al., "Neurokinin-1 receptors on lumbar spinothalamic neurons in the rat," *Neuroscience* 72:255-263 (1996).

McCarson and Krause, "The formalin-induced expression of tachykinin peptide and neurokinin receptor message RNAs in rat sensory ganglia and spinal cord is mediated by opiate preadministration," *Neuroscience* 64:729-739 (1995).

Munro et al., "The effects of neurokinin receptor antagonists on mustard oil-evoked activation of rat dorsal horn neurons," *Neuropeptides* 25:299-305 (1993).

Nagy et al., "NK1 and NK2 receptors contribute to C-fibre evoked slow potentials in the spinal cord," *NeuroReport* 5:2105-2108 (1994).

Nagy et al., "The role of neurokinin and N-methyl-D-aspartate receptors in synaptic transmission from capsaicin-sensitive primary afferents in the rat spinal cord in vitro," *Neuroscience* 52:1029-1037 (1993).

Nakaya et al., "Immunohistochemical localization of substance P receptor in the central nervous system of the adult rat," *J. Comp. Neurol.* 347:249-274 (1994).

Neugebauer et al., "Involvement of substance P receptors in the hyperexcitability of dorsal horn neurons during the development of acute arthritis in rat's knee joint," *J. Neurophysiol.* 73:1574-1583 (1995).

Neugebauer et al., "The involvement of substance P and neurokinin-1 receptors in the responses of rat dorsal horn neurons to noxious but not to innocuous mechanical stimuli applied to the knee joint," *Brain Res.* 666:207-215 (1994).

Nichols, et al., "Transmission of chronic nociception by spinal neurons expressing the substance P receptor," *Science* 286:1558-1561 (1999).

Picard et al., "Cardiovascular and behavioural effects of centrally administered tachykinins in the rat: characterization of receptors with selective antagonists," *Br. J. Pharmacol.* 112(1):240-249 (1994).

Quartu et al., "Calcitonin gene-related peptide in the human trigeminal sensory system at developmental and adult life stages: immunohistochemistry, neuronal morphometry and coexistence with substance P," *J. Chem. Neuroanat.* 5:143-157 (1992).

Salter et al., "Responses of functionally identified neurons in the dorsal horn of the cat spinal cord to substance P, neurokinin A and physalaemin," *Neuroscience* 43:601-610 (1991).

Sann et al., "Reduction of substance P bindling sites in the spinal dorsal horn after perineural capsaicin treatment in the rat," *Neurosci Lett.* 190:151-154 (1995).

Schaible et al., "Release of immunoreactive substance P in the spinal cord during development of acute arthritis in the knee joint of the cat: a study with antibody microprobes," *Brain Research* 529:214-223 (1990).

Simone et al., "Neural mechanisms of hyperalgesia," *Curr. Opin. Neurobiol.* 2:479-483 (1992).

Simone et al., "Neurogenic hyperalgesia: central neural correlates in responses of spinothalmic tract neurons," *J. Neurophysiol.* 66:228-246 (1991).

Smith et al., "Non-specific effects of the tachykinin NK1 receptor antagonist, CP-99, 994, in antinociceptive tests in rat, mouse and gerbil," *Eur. J. Pharmacol.* 271:481-487 (1994).

Stirpe et al., "Ribosome-inactivating proteins from plants: present status and future prospects," *Bio/Technology* 10:405-412 (1992).

Stirpe et al., "Ribosome-inactivating proteins from the seeds of *Saponario officinalis* L. (soapwort) of *Agrostemma githago* L. (corn cockle) and of *Asparagus officinalis* (asparagus) and from the latex of *Hura crepitans* L. (sandbox tree)." *Biochem J.* 216:617-625 (1983).

Tadano et al., "Immunohistochemical determination of rat spinal cord substance P, and antinociceptive effect during development of thiamine deficiency," *Brain Res.* 696:21-29 (1995).

Traub et al., "The spinal contribution of substance P to the generation and maintenance of inflammatory hyperalgesia in the rat," *Pain* 67:151-161 (1996).

Vigna et al., "Characterization of antibodies to the rat substance P (NK-1) receptor and to a chimeric substance P receptor expressed in mammalian cells," *J. Neurosci.* 14:834-845 (1994).

Yamamoto et al., "Effects of FK224, a novel cyclopeptide NK1 and NK2 antagonist, and CP-96, 345, a nonpeptide NK1 antagonist, on development and maintenance of thermal hyperesthesia evoked by carrageenan injection in the rat paw," *Anesthesiology* 79:1042-1050 (1993).

Yashpal et al., "Noxious peripheral stimulation produced antinociception mediated via substance P and opiod mechanisms in the rat tail-flick test," *Brain Res.* 674:97-103 (1995).

Yashpal et al., "Noxious stimulation decreases substance P binding in rat spinal dorsal horn: competition by endogenous ligand?" *NeuroReport* 5:2101-2104 (1995).

* cited by examiner

FIG. 12A

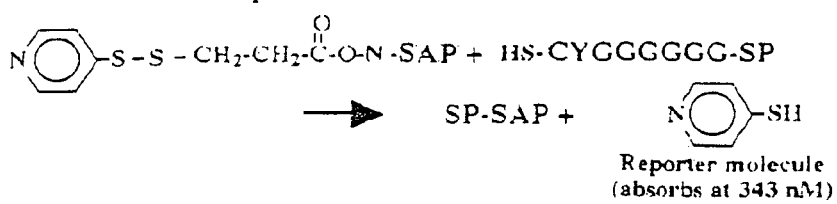

Reporter molecule
(absorbs at 343 nM)

FIG. 12B

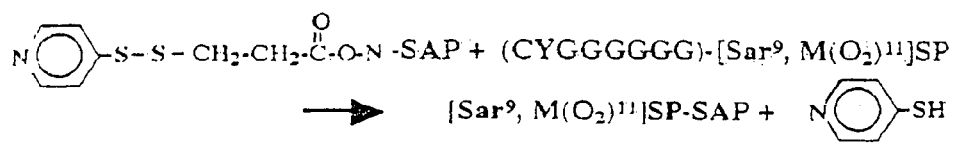

FIG. 12C

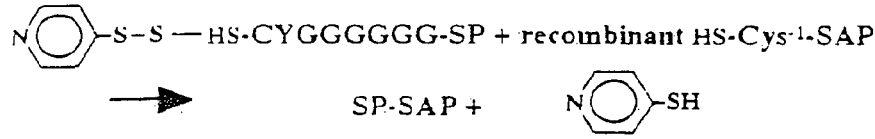

FIG. 12D

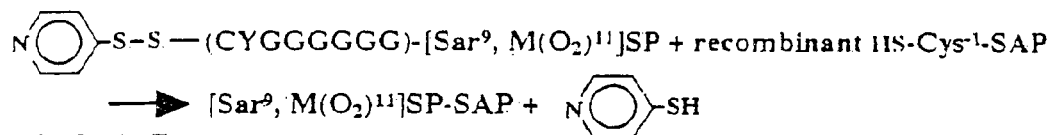

FIG. 12E

E) a recombinant form of saporin and substance P expressed in a recombinant protein expression system with the sequence of saporin, an appropriate linker and substance P that terminates with an additional glycine after Met[11]. The purified expressed protein is then converted to the amide with an appropriate enzyme, e.g., peptidylglycine-a-amidating monooxygenase

US 7,741,435 B2

SUBSTANCE P-SAPORIN (SP-SAP) CONJUGATES AND METHODS OF USE THEREOF

CROSS-REFERENCE TO RELATED APPLICATIONS

This application is a continuation of U.S. Ser. No. 09/523,790, filed Mar. 13, 2000, now abandoned which is a continuation-in-part of U.S. Ser. No. 08/890,157, filed Jul. 9, 1997, now U.S. Pat. No. 6,063,758, issued May 16, 2000 and which is incorporated herein by reference in its entirety.

Throughout this application, various publications may be referenced by Arabic numerals in parenthesis. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Many neurons synthesize and secrete small peptides that act on specific postsynaptic receptors and modify the activity of target neurons. Specific receptor molecules have been identified by binding studies and in some cases, such as the neurokinin-1 receptor (NK-1R) for Substance P (SP), the receptor has been cloned and sequenced. The NK-1R is found in many locations thought to be postsynaptic to SP-secreting terminals such as the cortical nucleus of the amygdala, striatum, locus coeruleus, rostral half of the nucleus ambiguous, nucleus tractus solitarius, dorsal motor nucleus of the vagus, intermediolateral cell column and lamina I and III of the dorsal horn of the spinal cord (1,2). Studies with agonists and antagonists indicate that most, if not all, of the effects of SP in the mammalian CNS are attributable to action at the G-protein coupled NK-1R (3).

A number of functional roles have been attributed to SP in keeping with anatomical studies (e.g. (3)) that show neurons expressing SP in a number of locations throughout the CNS, PNS and gut. For example, experiments utilizing injections of SP into the lateral ventricles have shown increases in blood pressure and heart rate as well as stereotyped behaviors such as face washing, grooming, and wet dog shakes (3). These autonomic manifestations are likely attributable to action in the medulla where prominent NK-1R expression has been demonstrated in the nucleus tractus solitarius, and stereotyped behaviors may reflect action in the basal ganglia and/or limbic system (1,4-6). The current state of knowledge, however, does not unambiguously identify the site of action for these and many other effects of SP. All of these actions are likely mediated through action of substance P at NK-1R (3,4).

The best known role for SP is in nociception. Small unmyelinated C-fibers of the PNS that are thought to be primary nociceptive neurons secrete SP and glutamate. Capsaicin, an agent that can destroy C-fibers, produces cutaneous analgesia and is approved for topical use to alleviate the pain of postherpetic neuralgia (Zostrix). Capsaicin injection of neonates has long been used to produce animals with no C-fibers and altered threshold to painful cutaneous stimuli. SP-containing nerve terminals are present in the spinal nucleus of the trigeminal nerve and the superficial layers of the spinal dorsal horn, areas known to be important in pain perception (1) and rich in NK-1R (1,2). In spite of the development of peptide and nonpeptide antagonists of NK-1R, considerable controversy remains about the precise role of SP acting at NK-1R in pain perception (7-17).

SUMMARY OF THE INVENTION

This invention provides conjugates comprising Substance P, or an analog thereof, and a protein that inhibits protein synthesis. The protein may be the ribosome-inactivating protein saporin (SAP).

This invention provides a method of reducing the perception of pain by a subject comprising administering to the subject an effective amount of the pharmaceutical composition of the conjugate comprising Substance P, or an analog thereof, and a protein that inhibits protein synthesis, so as to reduce the perception or pain by the subject. The protein may be the ribosome-inactivating protein SAP.

This invention provides a method of selectively destroying NK-1 receptor expressing cells in a subject comprising administering to the subject an effective amount of the conjugate comprising Substance P, or an analog thereof, and a protein that inhibits protein synthesis, so as to selectively destroy NK-1R-expressing cells. The protein may be ribosome-inactivating protein SAP.

This invention also provides a method for treating a NK-1 receptor associated disorder in a subject, which comprises administering to the subject an amount of the pharmaceutical composition comprising Substance P, or an analog thereof, and a protein that inhibits protein synthesis, to thereby treat a disorder associated with the NK-1R. The protein may be the ribosome-inactivating protein SAP.

BRIEF DESCRIPTION OF THE FIGURES

FIG. 12A-E: Synthesis of Substance P—Saporin, (SEQ ID Nos. 3 and 4).

DETAILED DESCRIPTION OF THE INVENTION

Figure 1:
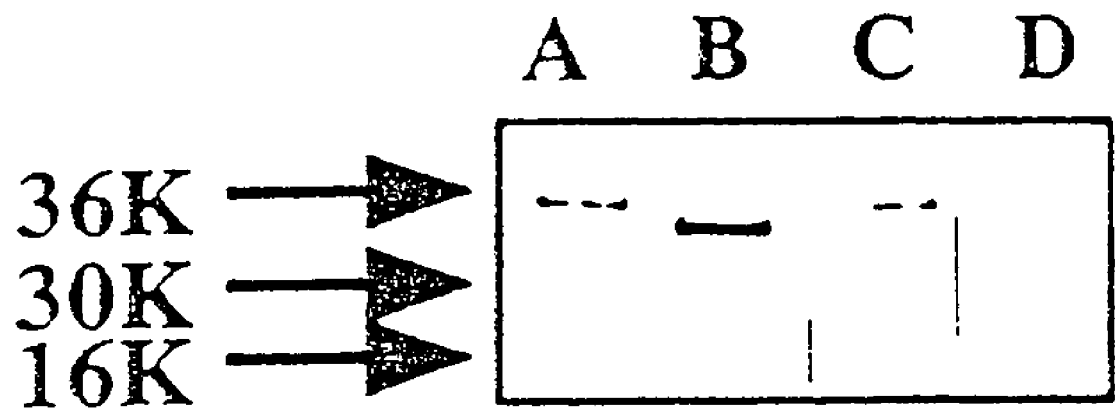
FIG. 1: Sodium dodecyl sulfate polyacrylamide gel electrophoresis of SP-SAP.

This invention provides a conjugate comprising Substance P and Saporin (SP-SAP). In one embodiment the conjugate comprises an analog of Substance P. In another embodiment the conjugate comprises an analog of Saporin.

This invention provides a conjugate comprising a Substance P analog having the amino acid sequence CYGGGGGGRPKPQQFFSarLMet (O$_2$)-amide (SEQ ID No. 1) and Saporin ([Sar$^9$, Met (O$_2$)$^{11}$]-SP-SAP). This invention provides a conjugate comprising a Substance P analog having the amino acid sequence at the N-terminus CYGGGGGGRPKPQQFFGLM-amide (SEQ ID No. 2) and Saporin (SP-SAP).

This invention provides a conjugate comprising Substance P and a ribosome-inactivating protein.

This invention provides a conjugate comprising a Substance P analog having the amino acid sequence CYGGGGGGGRPKPQQFFSarLMet ($O_2$)-amide and a ribosome-inactivating protein. In one embodiment the ribosome-inactivating protein is ricin A chain, gelonin, pokeweed antiviral protein, or a bacterial toxin that inhibits protein synthesis, such as diphtheria toxin or *pseudomonas aeruginosa* toxin or fragments thereof.

This invention provides a conjugate comprising a Substance P analog having the amino acid sequence CYGGGGGGGRPKPQQFFGLM-amide and a ribosome-inactivating protein. In one embodiment the ribosome-inactivating protein is ricin A chain, gelonin, pokeweed antiviral protein, or a bacterial toxin that inhibits protein synthesis, such as diphtheria toxin or pseudomonas aeruginosa toxin or fragments thereof.

Substance P can be attached to Saporin through a chemical bond, or the composition can be prepared as a chimera using techniques of recombinant DNA. The conjugate can be used to treat Substance P–, or an analog thereof, mediated pathophysiological conditions by specifically targeting cells having Substance P, or an analog thereof, receptors and inhibiting proliferation of or causing death of such cells. Additionally, the conjugate can be used to target cytotoxic agents into cells having Substance 2, or an analog thereof, receptors to inhibit the proliferation of such cells. Saporin and Saporin derivatives are known to the skilled in the art. Saporin is a potent ribosome-inactivating protein (RIP) which s isolated from the seeds of the plant *Saponaria officinalis* (18).

This invention provides a fusion protein comprising the amino acid sequence encoding Substance P and Saporin. This invention provides a recombinant nucleic acid molecule comprising an isolated nucleic acid molecule encoding Substance P and Saporin.

In one embodiment Saporin is conjugated to an agent. Such agents include but are not limited to the following: alkaline phosphatase, beta-galactosidase, glucose-6-phosphate dehydrogenase, maleate dehydrogenase and peroxidase, chemiluminescent agents which include luminol, isoluminol, aromatic acridinium esters, imidazoles, acridinium salts, and oxalate esters. Similarly, bioluminescent compounds may be utilized for labeling, the bioluminescent compounds including luciferin, luciferase, and aequorin.

In another embodiment Saporin is conjugated to an antibody. An antibody, polypeptide or isolated nucleic acid molecule may be labeled with a detectable marker including, but not limited to: a radioactive label, or a colorimetric, a luminescent, or a fluorescent marker, or gold. Radioactive labels include, but are not limited to: $^3$H, $^{14}$C, $^{32}$P, $^{33}$p, $^{35}$S, $^{36}$Cl, $^{51}$Cr, $^{57}$Co, 59Co, $^{59}$Fe, $^{90}$Y, $^{125}$I, $^{131}$I, and $^{186}$Re. Fluorescent markers include, but are not limited to: fluorescein, rhodamine and auramine. Colorimetric markers include, but are not limited to: biotin, and digoxigenin. Further, the antibody, polypeptide or nucleic acid molecule may be detected by a second antibody that may be linked to an enzyme, such as alkaline phosphatase or horseradish peroxidase. Other enzymes which may be employed are well known to one of ordinary skill in the art.

Antibodies or antibody fragments that would be useful would be antibodies to the NK-1R. Antibody fragments useful in the present invention include F(abi)2, F(ab)2, Fabi, Fab, Fv and the like including hybrid fragments. Preferred fragments are Fabi, F(abi)2, Fab, and F(ab)2. Also useful are any subfragments retaining the hypervariable, antigen-binding region of an immunoglobulin and having a size similar to or smaller than a Fabi fragment. This will include genetically engineered and/or recombinant proteins, whether single-chain or multiple-chain, that incorporate an antigen binding site and otherwise function in vivo as targeting vehicles in substantially the same way as natural immunoglobulin fragments. Fabi antibody fragments may be conveniently made by reductive cleavage of F(abi)2 fragments, which themselves may be made by pepsin digestion of intact immunoglobulin. Fab antibody fragments may be made by papain digestion of intact immunoglobulin, under reducing conditions, or by cleavage of F(ab)2 fragments which result from careful papain digestion of whole immunoglobulin. The fragments may also be produced by genetic engineering.

Antibodies against tumor antigens and against pathogens are known. For example, antibodies and antibody fragments that specifically bind markers produced by or associated with tumors or infectious lesions, including viral, bacterial, fungal and parasitic infections, and antigens and products associated with such microorganisms. In particular, antibodies against an antigen, e.g., a gastrointestinal, lung, breast, prostate, ovarian, testicular, brain or lymphatic tumor, a sarcoma or a melanoma, are advantageously used.

This invention provides a pharmaceutical composition comprising a therapeutically effective amount of the conjugate comprising Substance P and Saporin (SP-SAP) and a pharmaceutically acceptable carrier.

This invention provides a pharmaceutical composition comprising a therapeutically effective amount of the conjugate comprising a Substance P analog having the amino acid sequence CYGGGGGGRPKPQQFFSarLMet ($O_2$)-amide (SEQ ID NO. 1) and a pharmaceutically acceptable carrier.

This invention provides a pharmaceutical composition comprising a therapeutically effective amount of the conjugate comprising a Substance P analog having the amino acid sequence CYGGGGGGRPKPQQFFGLM-amide (SEQ ID NO. 2) and Saporin and a pharmaceutically acceptable carrier.

This invention provides a pharmaceutical composition comprising a therapeutically effective amount of the conjugate comprising Substance P and a ribosome-inactivating protein and a pharmaceutically acceptable carrier.

This invention provides a pharmaceutical composition comprising a therapeutically effective amount of the conjugate comprising a Substance P analog having the amino acid sequence CYGGGGGGRPKPQQFFSarLMet ($O_2$)-amide (SEQ ID NO. 1) and a ribosome-inactivating protein and a pharmaceutically acceptable carrier. In one embodiment the ribosome-inactivating protein is ricin A chain, gelonin, pokeweed antiviral protein, or a bacterial toxin that inhibits protein synthesis, such as diphtheria toxin or pseudomonas aeruginosa toxin or fragments thereof.

This invention provides a pharmaceutical composition comprising a therapeutically effective amount of the conjugate comprising a Substance P analog having the amino acid sequence CYGGGGGGRPKPQQFFGLM-amide (SEQ ID NO. 2) and a ribosome-inactivating protein and a pharmaceutically acceptable carrier. In one embodiment the ribosome-inactivating protein is ricin A chain, gelonin, pokeweed antiviral protein, or a bacterial toxin that inhibits protein synthesis, such as diphtheria toxin or pseudomonas aeruginosa toxin or fragments thereof.

In one embodiment the pharmaceutical composition further comprises a cytokine. Examples of cytokines include but are not limited: transforming growth factor beta, epidermal growth factor family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors.

This invention provides a method of reducing/alleviating/decreasing the perception of pain by a subject comprising administering to the subject an effective amount of the pharmaceutical composition comprising a therapeutically effective amount of the conjugate comprising Substance P and Saporin (SP-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGRPKPQQFFSarLMet($O_2$)-amide (SEQ ID NO. 1) and Saporin ([$Sar^9$, Met ($O_2$)$^{11}$]-SP-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGRPKPQQFFGLM-amide (SEQ ID NO. 2) and Saporin (SP-SAP) and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGRPKPQQFFSarLMet($O_2$)-amide (SEQ ID NO. 1) and a ribosome-inactivating protein and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising a Substance P analog which has the amino acid sequence CYGGGGGGRPKPQQFFGLM-amide (SEQ ID NO. 2) and a ribosome-inactivating protein and a pharmaceutically acceptable carrier so as to reduce the perception of pain by the subject.

This invention provides a method of reducing the perception of pain by a subject comprising administering to the subject an effective amount of the pharmaceutical composition comprising a therapeutically effective amount of the conjugate comprising Substance P and a ribosome-inactivating protein and a pharmaceutically acceptable carrier so as to reduce the perception of pain by the subject. In one embodiment the ribosome-inactivating protein is ricin A chain, gelonin, pokeweed antiviral protein, or a bacterial toxin that inhibits protein synthesis, such as diphtheria toxin, pseudomonas aeruginosa toxin or fragments thereof.

This invention provides conjugates of Substance P and analogs of Saporin. For example, analogs of Saporin include but are not limited to Cys$^{-1}$-SAP, and Gly-SAP. An analog according to the present invention may be an analog of gelonin. An analog according to the present invention may be an analog of barley ribosome-inactivating protein. An analog according to the present invention may be an analog of momordin II. The present invention also provides a polynucleotide encoding an analog of a Type I ribosome-inactivating protein. The present invention also provides an agent toxic to a cell including an analog of a Type I ribosome-inactivating protein linked by a disulfide bond through a cysteine to a molecule which specifically binds to the cell, which cysteine is at an amino terminus of the analog.

Substance P, or an analog thereof, can be used to target the cytotoxic agent to cells expressing Substance P receptors in order to cause cell death.

This invention provides a method of selectively destroying NK-1R-expressing cells in a subject comprising administering to the subject an effective amount of the pharmaceutical composition comprising a therapeutically effective amount of the conjugate comprising Substance P and Saporin and a pharmaceutically acceptable carrier so as to selectively destroy NK-1-expressing cells.

This invention provides a method of selectively destroying NK-1R-expressing cells in a subject comprising administering to the subject an effective amount of the pharmaceutical composition comprising a therapeutically effective amount of the conjugate comprising a substance P analog such as [$Sar^9$, Met ($O_2$)$^{11}$]-SP or SP and Saporin and a pharmaceutically acceptable carrier so as to selectively destroy NK-1R-expressing cells.

This invention provides a method of selectively destroying NK-1R-expressing cells in a subject comprising administering to the subject an effective amount of the pharmaceutical composition comprising a therapeutically effective amount of the conjugate comprising a substance P analog such as [$Sar^9$, Met ($O_2$)$^{11}$]-SP or SP and a ribosome-inactivating protein and a pharmaceutically acceptable carrier so as to selectively destroy NK-1R-expressing cells. In one embodiment the ribosome-inactivating protein is ricin A chain, gelonin, pokeweed antiviral protein, or a bacterial toxin that inhibits protein synthesis, such as diphtheria toxin, pseudomonas aeruginosa toxin or fragments thereof.

This invention provides a method of treating a subject with cancer comprising administering to the subject an effective amount of the pharmaceutical composition comprising a therapeutically effective amount of the conjugate comprising a substance P analog such as [$Sar^9$, Met ($O_2$)$^{11}$]-SP or Substance P and Saporin and a pharmaceutically acceptable carrier so as to treat the cancer.

This invention provides a method of treating a subject with cancer comprising administering to the subject an effective amount of the pharmaceutical composition comprising a therapeutically effective amount of the conjugate comprising a substance P analog such as [$Sar^9$, Met ($O_2$)$^{11}$]-SP or SP and Saporin and a pharmaceutically acceptable carrier so as to treat the cancer.

This invention provides a method of treating a subject with cancer comprising administering to the subject an effective amount of the pharmaceutical composition comprising a therapeutically effective amount of the conjugate comprising a substance P analog such as [$Sar^9$, Met ($O_2$)$^{11}$]-SP or SP and a ribosome-inactivating protein and a pharmaceutically acceptable carrier so as to treat the cancer. In one embodiment the ribosome-inactivating protein is ricin A chain, gelonin, pokeweed antiviral protein, or a bacterial toxin that inhibits protein synthesis, such as diphtheria toxin, pseudomonas aeruginosa toxin or fragments thereof.

This invention provides a method for treating a NK-1R-associated disorder in a subject, which comprises administering to the subject an amount of the pharmaceutical composition comprising a therapeutically effective amount of the conjugate comprising Substance P and Saporin and a pharmaceutically acceptable carrier thereby treating the disorder associated with the NK-1R.

This invention provides a method for treating a NK-1R-associated disorder in a subject, which comprises administering to the subject an amount of the pharmaceutical composition comprising a therapeutically effective amount of the conjugate comprising a Substance P analog such as [$Sar^9$, $Met (O_2)^{11}$]-SP or SP and Saporin and a pharmaceutically acceptable carrier thereby treating the disorder associated with the NK-1R.

This invention provides a method for treating a NK-1R-associated disorder in a subject, which comprises administering to the subject an amount of the pharmaceutical composition comprising a therapeutically effective amount of the conjugate comprising a Substance P analog such as [$Sar^9$, $Met (O_2)^{11}$]-SP or SP and a ribosome-inactivating protein and a pharmaceutically acceptable carrier thereby treating the disorder associated with the NK-1R. In one embodiment the ribosome-inactivating protein is ricin A chain, gelonin, pokeweed antiviral protein, or a bacterial toxin that inhibits protein synthesis, such as diphtheria toxin, pseudomonas aeruginosa toxin or fragments thereof.

These disorders or diseases include but are not limited to: respiratory conditions (e.g. asthma, allergic rhinitis), ophthalmic conditions (e.g. conjunctivitis), cutaneous conditions (e.g. allergic dermatitis, dermatitis by contact, psoriasis), intestinal conditions (e.g. ulcerative colitis, Crohnis disease), gastrointestinal tract, central nervous system disorders such as anxiety and psychosis, inflammatory diseases such as rheumatoid arthritis and inflammatory bowel diseases, as well as pain in any of the aforesaid conditions, including migraine.

Other disorders or diseases include but are not limited to: Alzheimeris disease, multiple sclerosis, attenuation of morphine withdrawal, cardiovascular changes, oedema, such as oedema caused by thermal injury, chronic inflammatory diseases such as rheumatoid arthritis, asthma/bronchial hyperactivity and other respiratory diseases including allergic rhinitis, inflammatory diseases of the gut including ulcerative colitis and Crohnis disease, ocular injury and ocular inflammatory diseases, proliferative vitreoretinopathy, irritable bowel syndrome and disorders of bladder function including cystitis and bladder detrusor hyperreflexia, demyelinating diseases such as multiple sclerosis and amyotrophic lateral sclerosis, asthmatic disease, small cell carcinomas, in particular small cell lung cancer, depression, dysthymic disorders, chronic obstructive airways disease, hypersensitivity disorders such as poison ivy, vasospastic diseases such as angina and Reynauldis disease, fibrosing, and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosis conjunctivitis, vernal conjunctivitis, contact dermatitis, atopic dermatitis, urticaria, and other eczematoid dermatitis and emesis; central nervous system disorders such as anxiety, depression, psychosis and schizophrenia; neurodegenerative disorders such as AIDS related dementia, senile dementia of the Alzheimer type, Alzheimeris disease and Downis syndrome; demyelinating diseases such as multiple sclerosis (MS) and amyotrophic lateral sclerosis (ALS; Lou Gehrigis disease) and other neuropathological disorders such as peripheral neuropathy inflammatory diseases such as inflammatory bowel disease, irritable bowel syndrome, psoriasis, fibrositis, ocular inflammation, osteoarthritis and rheumatoid arthritis, allergies such as eczema and rhinitis; hypersensitivity disorders such as poison ivy; ophthalmic diseases such as conjunctivitis, vernal conjunctivitis, dry eye syndrome, and the like; cutaneous diseases such as contact dermatitis, atopic dermatitis, urticaria, and other eczematoid dermatitis; oedema; such as oedema caused by thermal injury; addition disorders such as alcoholism; stress related somatic disorders; reflex sympathetic dystrophy such as shoulder/hand syndrome; dysthymic disorders; neuropathy, such as diabetic or peripheral neuropathy and chemotherapy-induced neuropathy; postherpetic and other neuralgias; asthma; osteoarthritis; rheumatoid arthritis; and especially migraine.

The subjects to be treated or whose tissue may be used herein may be a mammal, or more specifically a human, horse, pig, rabbit, dog, cat, monkey, or rodent. In the preferred embodiment the subject is a human.

The invention includes the pharmaceutically acceptable salts and complexes of all the compounds described herein. The salts include but are not limited to the following acids and bases. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet. In a further embodiment, the pharmaceutical carrier is a gel and the pharmaceutical composition is in the form of a suppository or cream. In a further embodiment, the compound may be formulated as part of a pharmaceutically acceptable transdermal patch.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric and polyhydric alcohols, e.g. glycols) and their derivatives, and oils (e.g. fractionated coconut oil and arachis oil) For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant, which are useful for intranasal administration.

Liquid pharmaceutical compositions which are sterile solutions or suspensions can be utilized for intramuscular, intrathecal, intratracheal, epidural, intraperitoneal or subcutaneous injections. Sterile solutions can also be administered intravenously. The compounds may be prepared as a sterile solid composition that may be dissolved or suspended at the time of administration using sterile water, saline, or other appropriate sterile injectable medium. Carriers are intended to include necessary and inert binders, suspending agents, lubricants, flavorants, sweeteners, preservatives, dyes and coatings.

The compound can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

Besides containing an effective amount of the compounds described herein the pharmaceutical compositions may also include suitable diluents, preservatives, solubilizers, emulsifiers, adjuvant and/or carriers.

The resulting pharmaceutical compositions may be liquids or lyophilized or otherwise dried formulations. Examples of suitable diluents include, but are not limited to, Tris-HCL, Tris-acetate and Tris-phosphate. The diluents employed may vary in their buffer contents pH and/or ionic strength. Examples of representative additives that may be used in the present invention include, but are not limited to: albumin or gelatin to prevent absorption to surfaces, detergents (e.g., Tween 20, Tween 80, Plurpnic F68, bile acid salts), solubilizing agents (e.g., Thimerosal, benzyl alcohol), bulking substances or tonicity modifiers (e.g., lactose, mannitol), covalent attachment of polymers such as polyethylene glycol to the protein, complexation with metal ions, or incorporation of the material into or onto particulate preparation of polymeric compounds such as polylactic acid, polyglycolic acid, polyvinyl pyrrolidone, etc. or into liposomes, microemulsions, micelles, unilamellar or multimeller vesicles, erythrocyte ghosts, or spheroplasts. Such compositions will influence the physical state, solubility, stability, rate of in vivo release, and rate of in vivo clearance of the compounds.

Examples of optional ingredients which may be included in the pharmaceutical compositions of the present invention include antioxidants, e.g., ascorbic acid; low molecular weight (less than about the residues) polypeptides, i.e., polyarginine or tripeptide; proteins, such as serum albumin, gelatin, or immunoglobulins; amino acids, such as glycine, glutamine acid, aspartic acid, or arginine; chelating agents such as EDTA; and sugar alcohols such as mannitol or sorbitol.

The choice of composition will depend on the physical and chemical properties of the compounds. Controlled or sustained release compositions include formulation of lipophilic deposits (e.g., fatty acids, waxes, oils). Also comprehended by the invention are particulate compositions coated with polymers (e.g., poloxamers or poloxamines) and compounds coupled to antibodies directed against tissue-specific receptors, ligands or antigens or coupled to ligands of tissue-specific receptors. Other embodiments of the compositions of the invention incorporate particulate forms of protective coatings, protease inhibitors or permeation enhancers for various routes of administration, including parenteral, pulmonary, nasal and oral.

Optimal dosages to be administered may be determined by those skilled in the art, and will vary with the particular compound in use, the strength of the preparation, the mode of administration, and the advancement of the disease condition. Additional factors depending on the particular subject being treated, including subject age, weight, gender, diet and time of administration, will result in a need to adjust dosages. Administration of the compound may be effected continuously or intermittently. in any treatment regimen, the composition may be administered to a patient either singly or in a cocktail containing two or more targeted toxins, other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine, and chloroquine. All of is these agents are administered in generally-accepted efficacious dose ranges such as those disclosed in the Physician's Desk Reference, 41st Ed., Publisher Edward R. Barnhart, N.J. (1987).

In the treatment, an appropriate dosage level will generally be about 0.001 to 50 mg per kg patient body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

This invention is further illustrated in the Experimental Details Sections that follow. These sections are set forth to aid in understanding the invention but are not intended to, and should not be construed to, limit in any way the invention as set forth in the claims that follow thereafter.

Experimental Details Sections

Development of a way to selectively destroy the NK-1R-expressing neurons not only would greatly enhance our understanding of the role of these neurons and SP in nociception, but also would reveal new approaches to the management of chronic, intractable pain. Similarly, selective lesioning of NK-1R-expressing neurons in the basal ganglia, medullary autonomic centers, the limbic system or gut would provide novel and useful information that would further our understanding of the function of SP in these locations as well as lead to possible therapeutic strategies. Moreover, the availability of specific, reversible antagonists and agonists for NK-1R and NK-3R would complement lesions made by a specific cytotoxin, and allow comparison of acute/reversible vs. chronic/irreversible impairment of NK-1R neuron activation. The advantages of NK-1R lesions would result from their long-term effects that would permit detailed physiological, neurochemical and behavioral analysis of changes produced by selective loss of NK-1R+ neurons. The short acting, reversible antagonists are available to confirm or validate the findings obtained with SP-SAP lesions, an important advantage when developing a novel experimental approach.

Cytotoxins that are specific for NK-1R-bearing cells were made. These cytotoxins are produced by conjugation of SP or [$Sar^9$, Met $(0_2)^{11}$]-SP, an agonist of SP, to saporin (SAP), a potent ribosome-inactivating protein. SP or its agonists bind to NK-1R, the conjugate is internalized, and SAP inactivates the neuronal protein synthesis mechanism, which results in cell death. The results indicate that spinal intrathecal injections of substance P-saporin (SP-SAP) or [$Sar^9$, Met $(0_2)^{11}$]-SP-SAP can be used to lesion NK-1R expressing neurons of the dorsal horn, and suggest that this lesion may decrease pain perception.

Synthesis of SP-SAP and [$Sar^9$, Met $(0_2)^{11}$]-SP-SAP: An N-terminal-extended form of SP was synthesized (Bio-Synthesis, Inc., Lewisville Tex.): CYGGGGGGRPKPQQFF-GLM-amide (SP) (SEQ ID NO. 2) or CYGGGGGGRPK-PQQFFSarLMet($0_2$)-amide ([$Sar^9$, Met $(0_2)^{11}$]-SP) (SEQ ID NO. 1). These analogs keep the C-terminal intact, as is required for SP activity; N-terminal modification is allowed (19). The N-terminal Cys possesses the free sulfhydryl which is able to react with pyridyl dithione-derivatized SAP. This creates a disulfide linkage that has been thought to be necessary in toxin conjugates (20). Saporin was derivatized with N-succinimidyl-3-[2-pyridyldithio]proprionate (SPDP) (21). The reaction product is heterogeneous, with a mixture of zero, one, two and three pyridyl dithio groups attached to SAP under the conditions used. As seen in Table 1, mono-derivatized SAP was able to be purified by the published protocol (21).

TABLE 1

Analysis of chromatographic fractions from ion-exchange purification of mono-derivatized saporin.

| fraction number (PT) (μm) | protein concentration(μM) protein/PT | pyridyl | ratio thione |
|---|---|---|---|
| 48 | 6.5 | 10.9 | 1.7 |
| 49 | 9.7 | 14.9 | 1.5 |
| 50 | 12.6 | 17.6 | 1.4 |
| 51 | 13.2 | 17.6 | 1.3 |
| 52 | 12.6 | 18.7 | 1.5 |
| 53 | 12.2 | 17.4 | 1.4 |
| 54 | 16.6 | 17.9 | 1.1 |
| 55 | 19.5 | 19.7 | 1.0 |
| 56 | 26.3 | 22.3 | 0.85 |
| 57 | 28.6 | 26.0 | 0.91 |
| 58 | 35.7 | 26.7 | 0.74 |
| 59 | 35.9 | 27.1 | 0.75 |
| 60 | 40.7 | 29.8 | 0.73 |
| 61 | 36.8 | 27.1 | 0.74 |
| 62 | 34.2 | 22.3 | 0.65 |
| 63 | 28.6 | 16.8 | 0.59 |
| 64 | 27.1 | 11.8 | 0.43 |
| 65 | 27.1 | 5.7 | 0.21 |
| 66 | 31.1 | 1.5 | 0.05 |
| Pool 56-61, | 32.0 | 32.1 | 1.0 |

A five-fold excess of SP or [$Sar^9$, Met $(0_2)^{11}$]-SP was added to the mono-derivatized SAP. Within 20 minutes, the reaction has gone to completion, as determined by pyridyl thiol release. Excess SP or [$Sar^9$, Met $(0_2)^{11}$]-SP is removed by extensive dialysis. Subsequent analysis by sodium dodecyl sulfate polyacrylamide gel is electrophoresis (SDS-PAGE) and Western blotting determined that the resulting product was a single molecule of SP or [$Sar^9$, Met $(0_2)^{11}$]-SP linked to a single SAP through a disulfide linkage (FIGS. 1 and 2).

Another method of synthesis is the use of a $Cys^{-1}$-SAP that is produced by recombinant means. This material is reduced by a reducing agent such as dithiothreitol and then purified from the reducing agent in a buffer that contains a low level of material that retains the sulfhydryl of the Cys-1 as the reduced form, such as, but not limited to, (ethylenedintrilo)-tetraacetic acid or its sodium salt. The Cys-1-SAP is then added to an excess quantity of an analog of substance P that is extended on the amino terminus and that contains a cysteine that is modified with a pyridyly thione group. An example of that, but not limited to, would be N(PyS)CYGGGGGGRPKPQQFF-GLM-amide (SEQ ID NO. 5).

Electrophoresis was performed with 16% Tricine gels in a mini-gel system (Bio-Pad, Richmond Calif.) according to the manufacturer's instructions. Transfer to nitrocelluse was performed with a Trans-Blot SD Semi-Dry Transfer Cell (Bio-Rad). Staining was as described (22). SP-SAP was electrophoresed and the migration compared to that of SAP. In FIG. 1, Lanes A and B are stained with Coomassie staining; lanes C and D are from Western blots using anti-SP. A) SP-SAP, B) SAP, C) SP-SAP, D) SP-SAP under reducing conditions. The migration of SP-SAP shows a single band with a slight increase in the molecular weight, accounted for by the molecular weight of the 18 amino acid peptide used for the conjugation. No free SAP is evident, nor any evidence of more than one SP per molecule of SAP. The Western blotting of the conjugate with an anti-SP antibody indicates that the higher molecular weight species contains SP. The staining is removed upon reduction of the conjugate, indicating that the SP is linked to SAP by a disulfide bond, as planned. While the molecular weight of SAP is 30,000 its migration in SDS-PAGE is aberrant because its high isoelectric point comprises binding with SDS (23).

Figure 2:
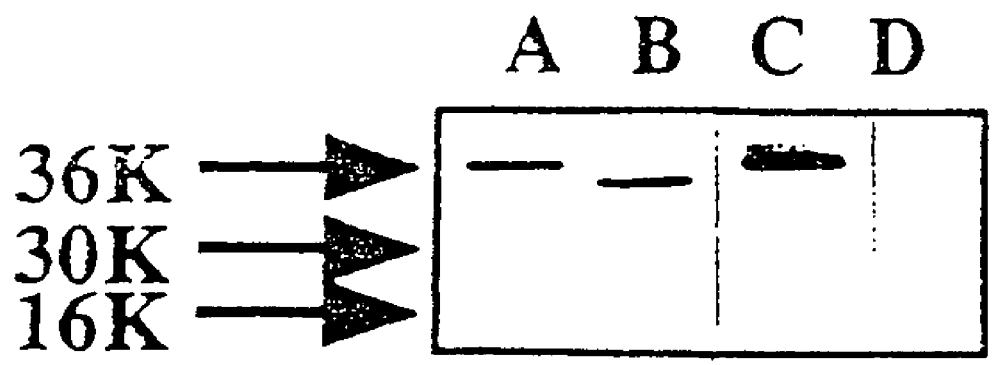
FIG. 2: Sodium dodecyl sulfate polyacrylamide gel electrophoresis of [Sar$^9$, Met (O$_2$)$^{11}$]-SP-SAP.

FIG. 2 shows electrophoresis of [$Sar^9$, Met $(0_2)^{11}$]-SP-SAP and SAP by methods described for FIG. 1. In FIG. 2 Lanes A and B are stained with Coomassie staining; lanes C and D are from Western blots using anti-SP. A) [Sar$^9$, Met (0$_2$)$^{11}$]-SP-SAP, B) SAP, C) [Sar$^9$, met (0$_2$)$^{11}$]-SP, D) [Sar$^9$, Met (0$_2$)$^{11}$]-SP-SAP under reducing conditions. The migration of [Sar$^9$, Met (0$_2$)$^{11}$]-SP-SAP shows a single band with a slight increase in the molecular weight, accounted for by the molecular weight of the 18 amino acid peptide used for the conjugation. No free SAP is evident, nor any evidence of more than one CYGGGGGG-[Sar$^9$, Met (0$_2$)$^{11}$]-SP (SEQ ID NO. 3) per molecule of SAP. The Western blotting of the conjugate with an anti-SP antibody indicates that the higher molecular weight species contains SP (SEQ ID NO. 3). The species is removed upon reduction of the conjugate, indicating that the CYGGGGGG-[Sar9,Met (02)11]-SP (SEQ ID NO. 3) is linked to SAP by a disulfide bond, as planned.

Figure 3:
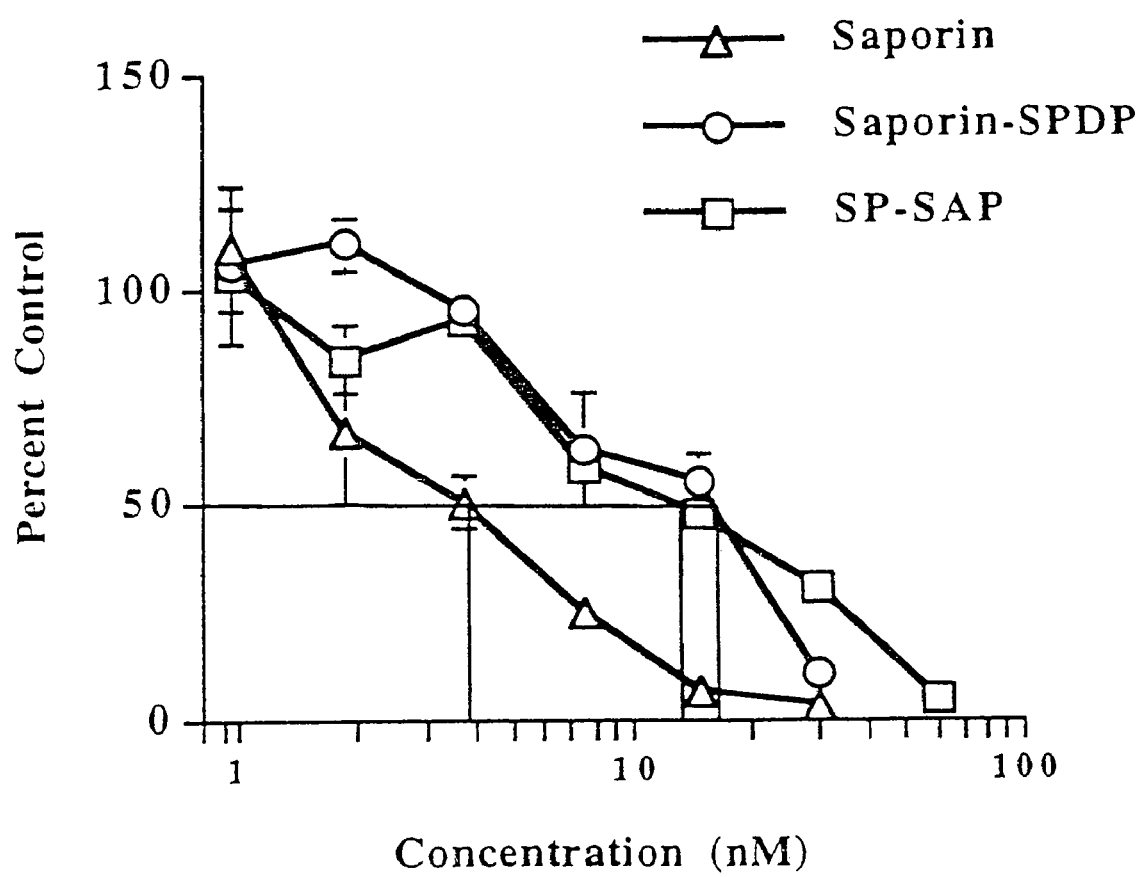
FIG. 3: Protein synthesis inhibition by saporin, derivatized saporin (SAP-SPDP) and SP-SAP.

SAP activity is measured by inhibition of production of the activity of luciferase by cell-free protein synthesis directed by luciferase mRNA. FIG. 3 shows the results *of this assay. This assay shows that SAP in the conjugate retains its protein synthesis inhibition activity, though there is a reduction on activity.

All reagents except samples are purchased from Promega (Madison Wis.). Reaction mixture consisted of 7 µl of rabbit reticulocyte lysate, 20 mM amino acids, 100 ng luciferase mRNA and sample at indicated concentrations in 10 µl volume. Reaction mixture is incubated for 30 minutes at 30° C. Relative light units are measured by Luciferase Assay Reagent in a Berthold Lumat LB9501 luminometer according to manufacturer's instructions.

In this assay, SAP has an ED$_{50}$ of approximately 4 pM. Comparison with literature values of saporin activity is favorable: reference (24), ED$_{50}$=30 pM, reference (22) ED$_{50}$=25 pM. Others (25) have shown that a mutein of SAP, Cys$^{-1}$-SAP, has equal activity to SAP.

Homogenate is prepared and binding performed as previously described (26). Briefly, iodinated SP at 150 pM is incubated in the presence of 100 nM of nonlabeled competitor (NKA: neurokinin A, NKB: neurokinin B). Membrane-bound label is separated from free label by centrifugation and measured with a gamma counter. Control is no addition of competitor.

Figure 4:
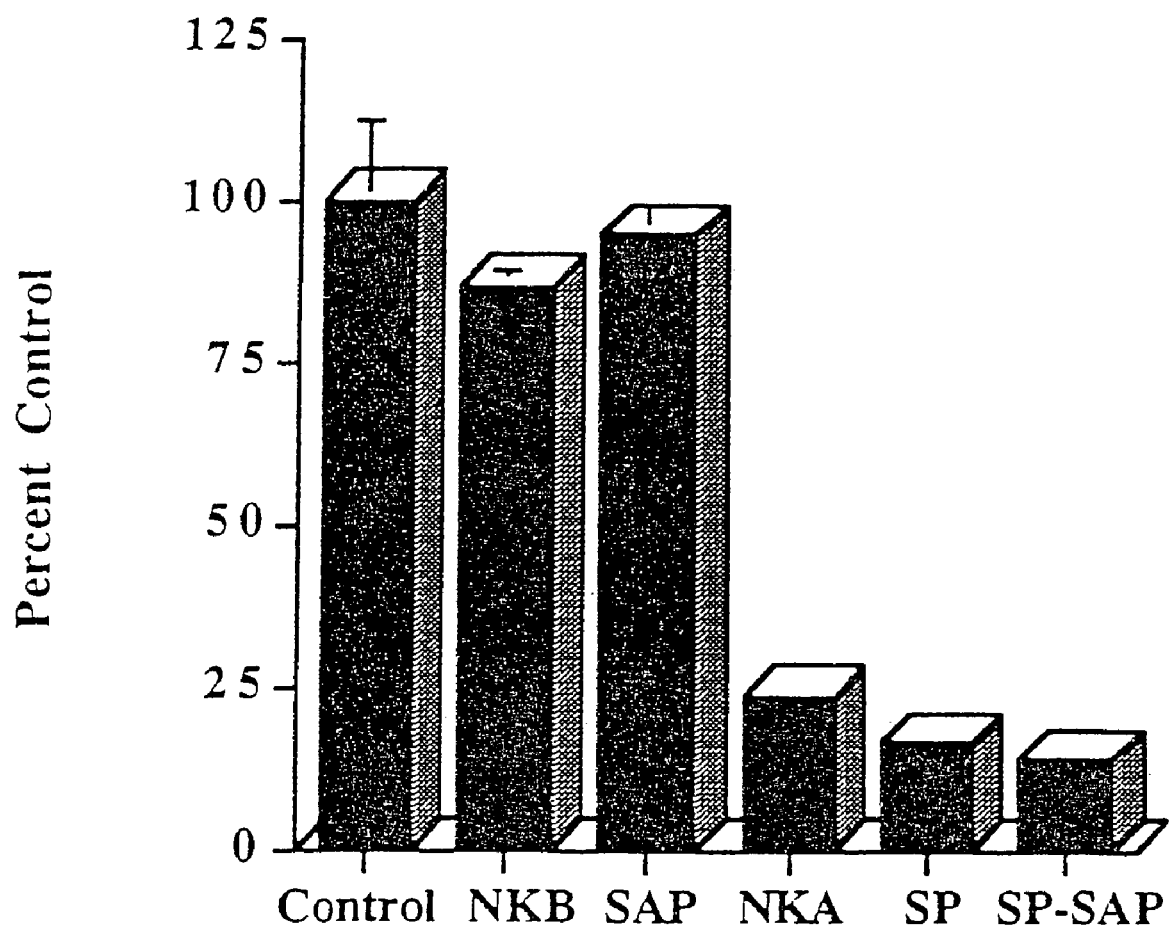
FIG. 4: Inhibition of radiolabeled SP binding to spinal cord membrane homogenates by SP-SAP.

The competitive effect of SP-SAP on SP binding is seen in FIG. 4. The inhibitory effect of the peptide toxin was very similar to that of SP. Binding specificity was shown with controls of SAP and neurokinin B, which showed little or no inhibition of iodinated SP binding (neurokinin A has significant interaction with the NK-1R in this assay). We conclude that SP-SAP retains complete binding to the NK-1R.

Figure 5:
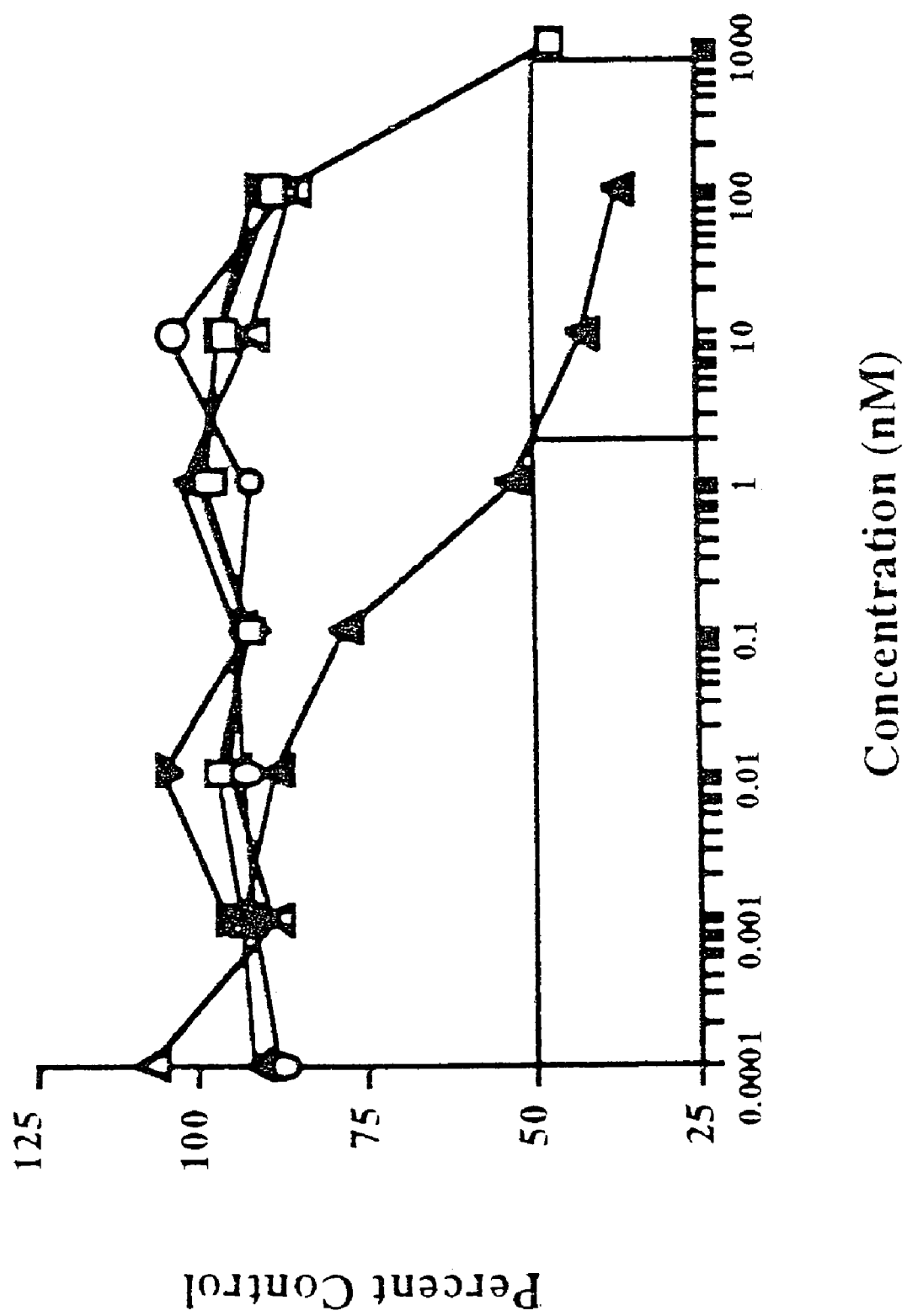
FIG. 5: Cytotoxicity of SP-SAP to KNRK cells and KNRK cells transfected with the NK-1 receptor.

Cytotoxicity Assay: Dr. Nigel Bunnett provided KNRK cells that have been transfected with the rat NK-1R (27). These cells express approximately 80,000 receptors that bind SP with a Kd of 6 nM (28). SP is internalized by the receptor in these cells. We tested SP-SAP against these cells and against KNRK cells that have not been transfected and that do not express the receptor. When challenged with SP-SAP, cytotoxicity is seen in a dose-dependent manner in the transfected cells; no cytotoxicity is seen at the same levels with the non-transfected cells (FIG. 5). The data reveals the potency of targeting SAP with Substance P. Because SAP has no method of internalization, it has a rather weak ED$_{50}$ of about 1 mM. Entrance to these cells by SAP is probably due to bulk-phase endocytosis. When targeted with substance P, SAP becomes approximately 500-fold more toxic (ED$_{50}$ of about 2 nM) to the target cells, while maintaining low toxicity to non-target cells.

Cells, either KNRK cells transfected with the NK-1R (28) or non-transfected KNRK cells (American Type Culture Collection, Rockville Md.) were plated at 2500 cells per 90 ?l in triplicate in wells of a 96-well plate. Cells were allowed to attach overnight and then samples were added at the indicated concentrations and incubated for 48 hours. MTS (Promega, Madison Wis.) and phenazine methosulfate (Sigma) were added according to distributoris (Promega) instructions and incubated for one hour. Optical density was measured at 490 nm and compared to standard wells with addition of phosphate-buffered saline. In the case of inhibition studies with anti-SP, anti-SP was preincubated with SP-SAP for 30 minutes before addition to cells. Standard deviation for all points was less then 10%. Additions to transfected cells: SP-SAP; SAP; SP; an equimolar mixture of SP and SAP. FIG. 5 shows SP-SAP addition to non-transfected KNRK cells.

Figure 6:
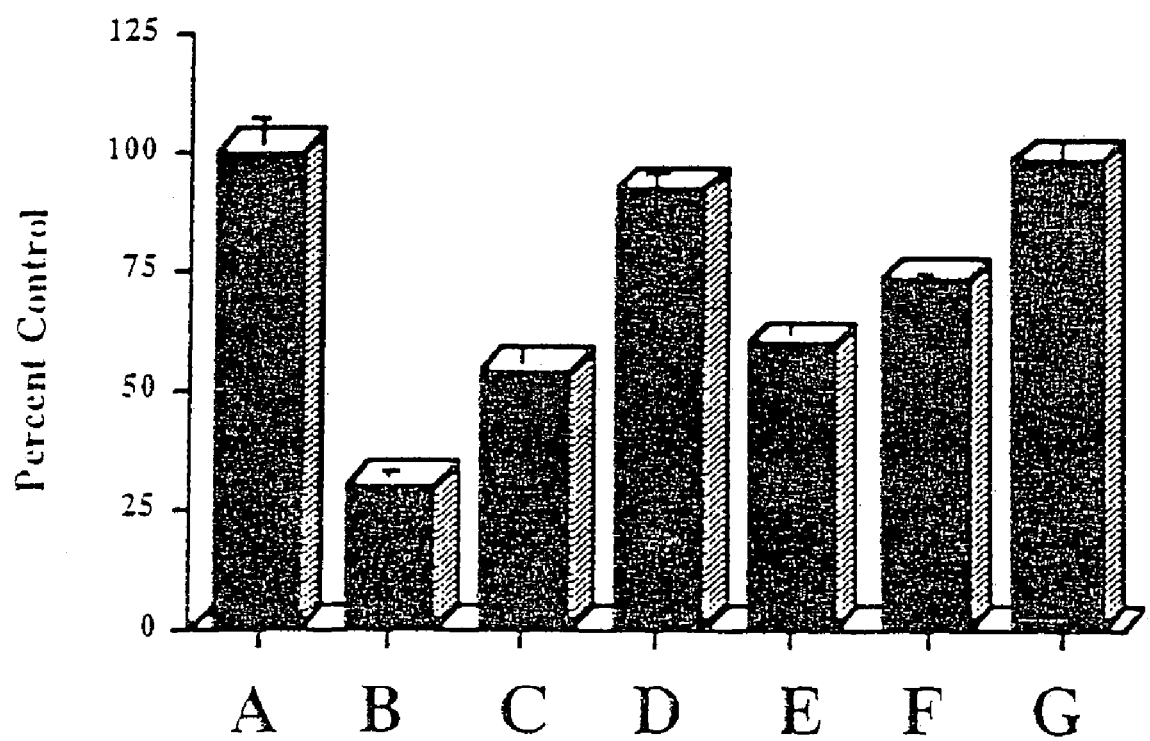
FIG. 6: Inhibition of SP-SAP demonstrates that cytotoxicity is mediated by SP.

KNRK cells transfected with the NK-1R were challenged as described in FIG. 5. As shown in FIG. 6, lane A: no addition control; B: 1 nM SP-SAP; C-G contain 1 nM SP-SAP; C: 0.1 µl anti-SP; D: 1 µl anti-SP; E: 0.1 mM SPa; F: 1 nM SPa. In G, SP-SAP was pre-incubated with 5 mM dithiothreitol for thirty minutes and then diluted for assay at 1 nM. In the case of competitive inhibition studies with peptide, peptide was added 30 minutes before SP-SAP. SPa is an N-terminal-extended analog of [Sar$^9$, Met (0$_2$)$^{11}$]-SP (19).

Further evidence that the cytotoxicity is mediated by SP is provided by more experiments with the NK-1R-bearing cells, seen in FIG. 6. Polyclonal rabbit anti-serum to SP inhibits, in a dose-dependent manner, the cytotoxicity of SP-SAP (FIG. 6C, D), presumably by interfering with the ability of SP to bind to its receptor. Excess agonist of SP is also able to inhibit the cytotoxicity in a dose-dependent manner (FIG. 6E, F). Finally, pretreatment of SP-SAP with a reducing agent, which will break the covalent bond between SP and SAP, completely eliminates the cytotoxicity. These data are powerful demonstrations that the cytotoxicity of SP-SAP is mediated through the binding and internalization of SP and the conjugated SAP by the NK-1R.

Figure 7:
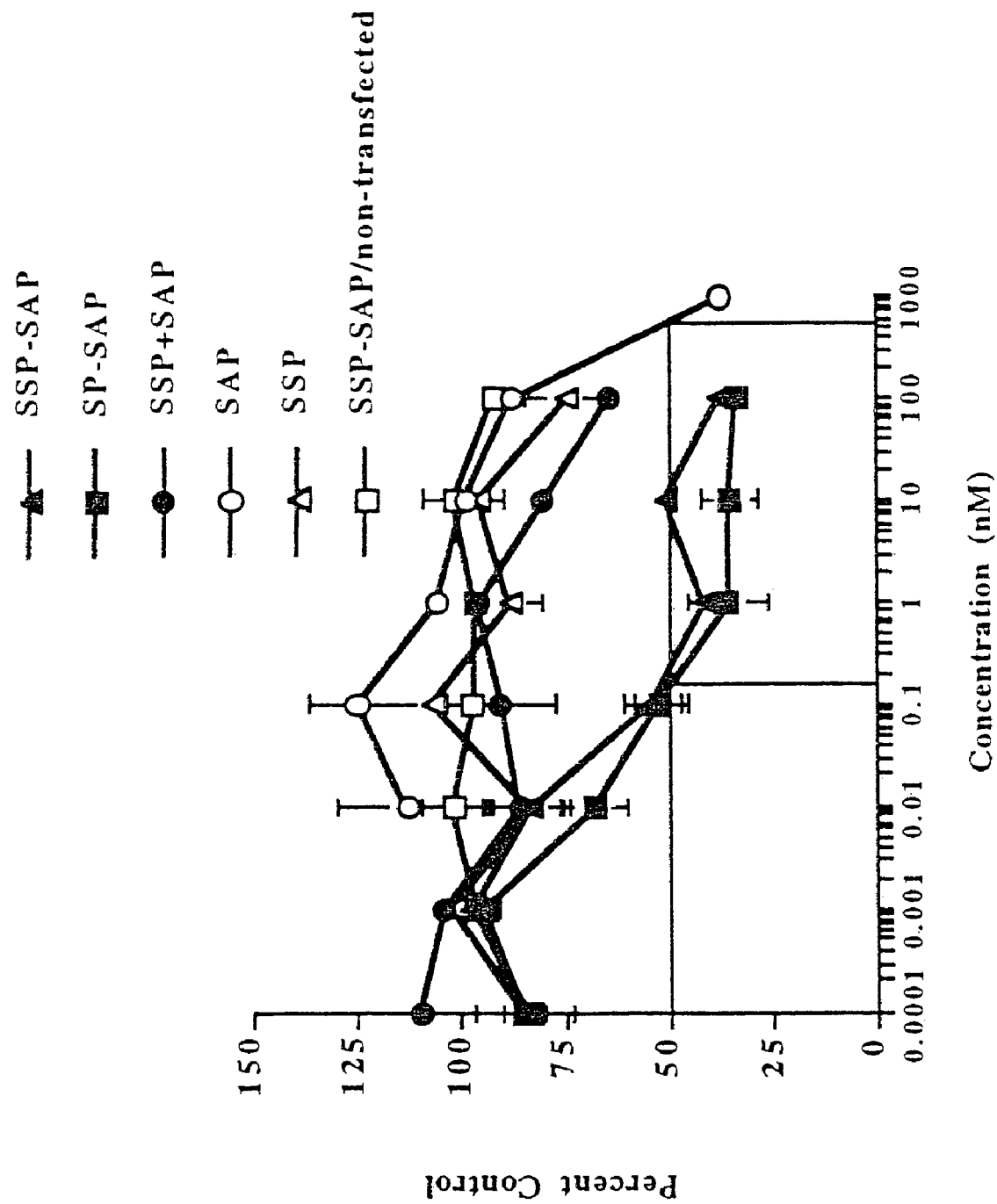
FIG. 7: Cytotoxicity of Stable SP-SAP to KNRK cells transfected with the NK-1R.

The cytotoxicity of [Sar$^9$, Met (0$_2$)$^{11}$]-SP-SAP to cells that express the NK-1R have been examined. Methods are the same for FIG. 5. The results are seen in FIG. 7. [Sar$^9$, Met (0$_2$)$^{11}$]-SP-SAP has similar cytotoxicity to NK-1R-expressing cells as SP-SAP. It has no effect on cells that do not express NK-1R. MTS (Promega) was added according to manufactureris instructions for one hour and absorbance at 490 nm was recorded and normalized to untreated control well values.

In vivo data has been obtained that shows the proposed construct, [Sar$^9$, Met (0$_2$)$^{11}$]-SP-SAP, is more active in vivo than SP-SAP, both after striatal and spinal intrathecal injections. Observations of rats with spinal intrathecal injections of [Sar$^9$, Met (0$_2$)$^{11}$]-SP-SAP show reduced sensitivity to painful stimuli.

FIG. 12 shows a recombinant form of saporin and substance P expressed in a recombinant protein expression system with the sequence of saporin, an appropriate linker and substance P that terminates with an additional glycine after Met$^{11}$. The purified expressed protein is then converted to the amide with an appropriate enzyme, e.g. peptidylglycine-a-amidating monoxygenase.

FIG. 12A is the actual procedure for the synthesis of SP-SAP. SP is Substance P, a peptide with the sequence: RPK-PQQFFGLM-amide (SEQ ID No. 4). 1 is the ribosome-inactivating protein saporin, from either the native source, *Saponoria officinalis*, or the recombinant form, derivatized with a reagent that introduces a sulfhydryl group such as 2-iminothiolane or pyryldithio-propionate. FIG. 12B is a procedure for the synthesis of [Sar$^9$, Met (0$_2$)$^{11}$]-SP-SAP. [Sar$^9$, Met (0$_2$)$^{11}$]SP is substance P with the amino acid sarcosine at position 9 and methionine at position 11. FIGS. 12C, 12D and 12E are methods for the synthesis of SP-SAP or [Sar$^9$, Met (0$_2$)$^{11}$]-SP-SAP. 2 is the recombinant saporin with a cysteine incorporated into the sequence.

1. Striatal Injections

Five adult, male Sprague-Dawley rats were pressure microinjected with [Sar$^9$, met (0$_2$)$^{11}$]-SP-SAP into the striatum. All rats were observed for open field ambulation; no consistent changes were observed after immunotoxin injection. Four rats were sacrificed and brain sections processed to analyze the effects of [Sar$^9$, Met (0$_2$)$^{11}$]-SP-SAP on striatal neurons. In all 4 rats, there was significant loss of neurons staining immunohistochemically for the NK-1R. In the 2 rats injected with 4.35 ng of [Sar$^9$, Met (0$_2$)$^{11}$]-SP-SAP, >90% of the striatal area in frontal sections through the injection site was devoid of NK-1R+ neurons. In one of the rats injected with 2.17 ng, the area devoid of NK-1R was 70-30% of the striatal area at the level of the injection site, but in the other rat, the injection site was medial and affected only the medial half of the striatum. In all 3 rats with accurate infections, the region of loss of NK-1R staining extended throughout the rostral-caudal extent of the striatum.

Neurons staining for choline acetyltransferase also were undetectable in the same region as that in which the NK-1R stain was absent. In sharp contrast, neurons stained for parvalbumin were present in abundance throughout the striata of injected rats. Indeed, neurons stained for parvalbumin could be seen within a few μM of the injection track. Cresyl violet-stained sections showed good preservation of normal striatal architecture. The only consistent lesion seen in cresyl violet-stained sections was the damage from the pipette track. These results with [Sar$^9$, Met (0$_2$)$^{11}$]-SP-SAP injections into the striatum show that [Sar$^9$, Met (0$_2$)$^{11}$]-SP-SAP is active in vivo.

These data indicate that Sar9, [Sar$^9$, Met (0$_2$)$^{11}$]-SP-SAP may be useful to eliminate NK-1R-expressing neurons. Thus, it may be useful to cause loss of some pain sensation. SP-SAP may be more useful for elimination of lamina 1 neurons of the dorsal horn and concomitant elimination of hyperalgesic pain. Both compounds may be useful in the elimination of acute hyperalgesic pain, depending on the dosage.

Experiments in Pain Models

A subpopulation of dorsal root ganglion neurons synthesize (29-32) and transport (33) substance P (SP) to the spinal cord, where it is released upon noxious stimulation of the innervated peripheral tissue (34-36). Although SP has been shown to excite spinal cord nociresponsive neurons (37,38), the role that SP and the substance P receptor (NK-1R) play in signaling nociceptive information remains unclear. In the normal animal, SP, upon release from primary afferents, diffuses to and interacts primarily with NK-1R-expressing neurons located in lamina I of the spinal cord (2,39-42). A high proportion of spinothalamic and spinobrachial neurons located in lamina I express NK-1R (43,44), suggesting that these NK-1R-expressing neurons play a role in the ascending conduction of nociceptive information.

To investigate the functions of lamina I NK-1R-expressing neurons in nociceptive signaling, we selectively ablated these neurons by infusing a cytotoxin conjugated to SP into the intrathecal space of the spinal cord in rats. When SP binds to spinal cord neurons expressing NK-1R, both SP and NK-1R are rapidly internalized (2,39-42). Using SP-induced internalization of NK-1R as a specific portal of entry into NK-1R-expressing spinal cord neurons, we armed SP with the ribosome-inactivating protein saporin (SAP). This substance P—saporin conjugate (SP-SAP), like other saporin conjugates, must be internalized to exert its toxicity as it inactivates and ultimately kills cells by blocking protein synthesis (23, 45). We performed a series of correlative in vitro and in vivo studies to determine the specificity and toxicity of SP-SAP, as well as functional changes in somatosensory processing.

SP-SAP internalization and cytotoxicity was examined in primary cultures of neonatal rat spinal cord neurons where approximately 15% of the neurons express NK-1R. All procedures were approved by Animal Care Committee at the VA Medical Center and the University of Minnesota. Neurons were cultured from the spinal cords of 18-day embryonic Holtzman rats (Harlan Sprague Dawley, Madison, Wis.). The whole spinal cord was dissected out of the rat and placed in 4° C. Puck's saline supplemented with 40 mM. glucose, 50 mM sucrose, and 10 mM Hepes (DISG media, pH 7.4). The spinal cords were then dissociated by trituration (15-20 times) through a small bore serological pipet. The resulting cell suspension was centrifuged at 4° C. for 5 min at 1500 rpm in a Sorvall RC-3B centrifuge (DuPont, Newtown, Conn.). The supernatant was removed and the pellet resuspended in Dulbecco's modified Eagle's medium (DMEM; Sigma Chemical Co., St. Louis, Mo.) plus 5% equine serum and 5% calf serum (v/v) (Hyclone, Logan, Utah). The cell suspension was plated on poly-L-ornithine coated 2-well chamber slides at a density of 100,000 cells/ml, and incubated at 37° C. with 9% CO$_2$. After 4 days the mitotic inhibitors, 5-fluoro-2'-deoxyuridine and uridine were added. At 7 days the media was replaced with DMEM plus 10% equine serum (v/v). The cells were incubated unil 14 days post-culture with media changes every 4th day.

At day 14 post-culture, either saline or SP, SP-SAP conjugate or saporin (SAP) were added to a final concentration of 10$^{-7}$ M. The cells were incubated for 12 hr with the SP-SAP or SAP compounds at which time the compounds were removed from the culture and fresh media was added. The cultures were then allowed to continue until the desired time-points (2 hr. 1, 4, 7, and 10 days) at which time the experiment was terminated and the cells were processed for immunohistochemistry by fixing for 20 min at 22° C. with 4% formalin in a phosphate buffered saline solution as previously described (2,39-42). Both SP (10$^{-7}$ M) and SP-SAP (10$^{-7}$ M) induced a rapid and similar degree of NK-1R internalization that was blocked by 5×10$^{-6}$ M of the non-peptide NK-1R antagonist RP67580. Two hours following treatment with 10$^{-7}$ M SP-SAP, but not 10$^{-7}$ M SAP, NK-1R internalization was visualized using an antibody that recognized NK-1R (FIG. 8A) and intracellular accumulation of SAP was visualized using an antibody that recognized SAP (FIG. 8B)

Figure 8:
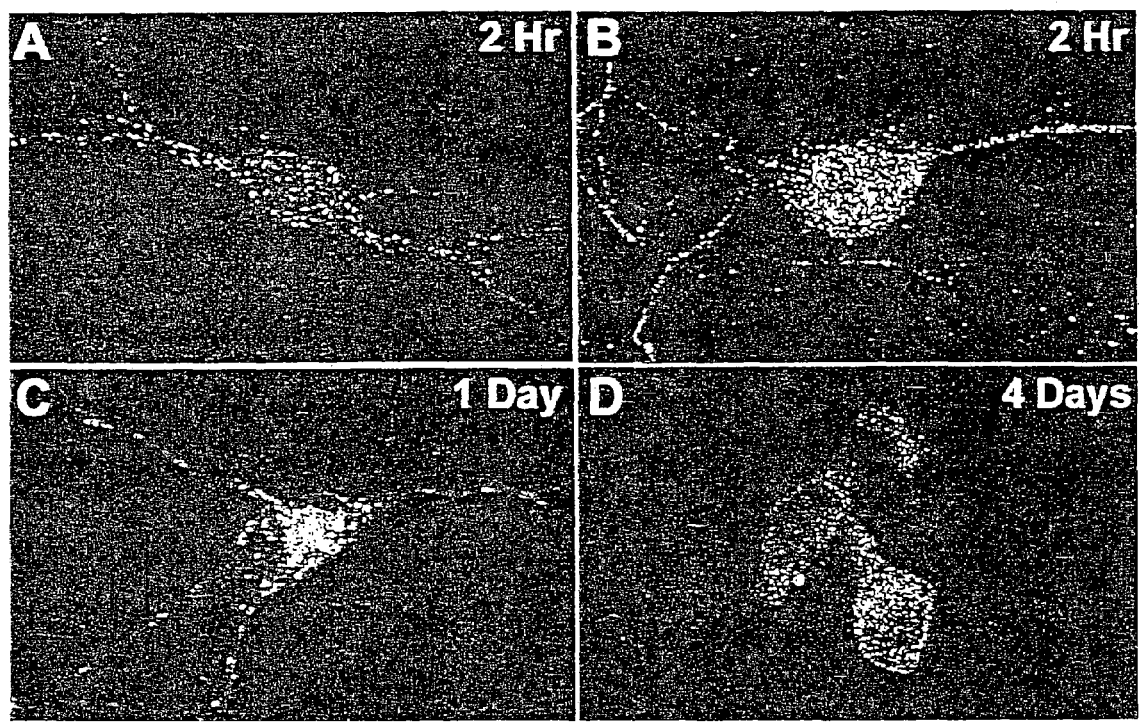
FIG. 8A-D: Internalization and cytotoxicity of SP-SAP in primary cultures of neonatal spinal cord neurons.

One day following SP-SAP treatment there was no significant loss of cultured N-1R-immunoreactive neurons although in the majority of these neurons the NK-1R immunoreactivity was localized within intracellular endosomes (FIG. 8C). In contrast, one day following treatment with SP alone the majority of NK-1R had recycled to the plasma membrane. Thus, within 24 hours after SP-SAP internalization these neurons could no longer efficiently recycle NK-1R back to the plasma membrane. Four days following SP-SAP treatment, there was an 82% decrease in the number of NK-1R-immunoreactive neurons, at seven days a 95% reduction, and at ten days there were no NK-1R-immunoreactive neurons remaining in culture. At four and seven days post-treatment the surviving NK-1R immunoreactive neurons showed shrunken cell bodies, diffuse NK-1R immunoreactivity throughout the cytoplasm (FIG. 8D), and shortened dendritic processes. In contrast, nearby neurons that did not express NK-1R immunoreactivity, but did express the neuronal marker, Microtubule Associated Protein-2 (MAP-2), appeared morphologically normal. Treatment of cultured spinal cord neurons with saline, SP or SAP alone resulted in no significant morphological or cytotoxic changes in either the NK-1R-expressing neurons or the non-NK-1R, MAP-2 immunofluorescent neurons.

Figure 9:
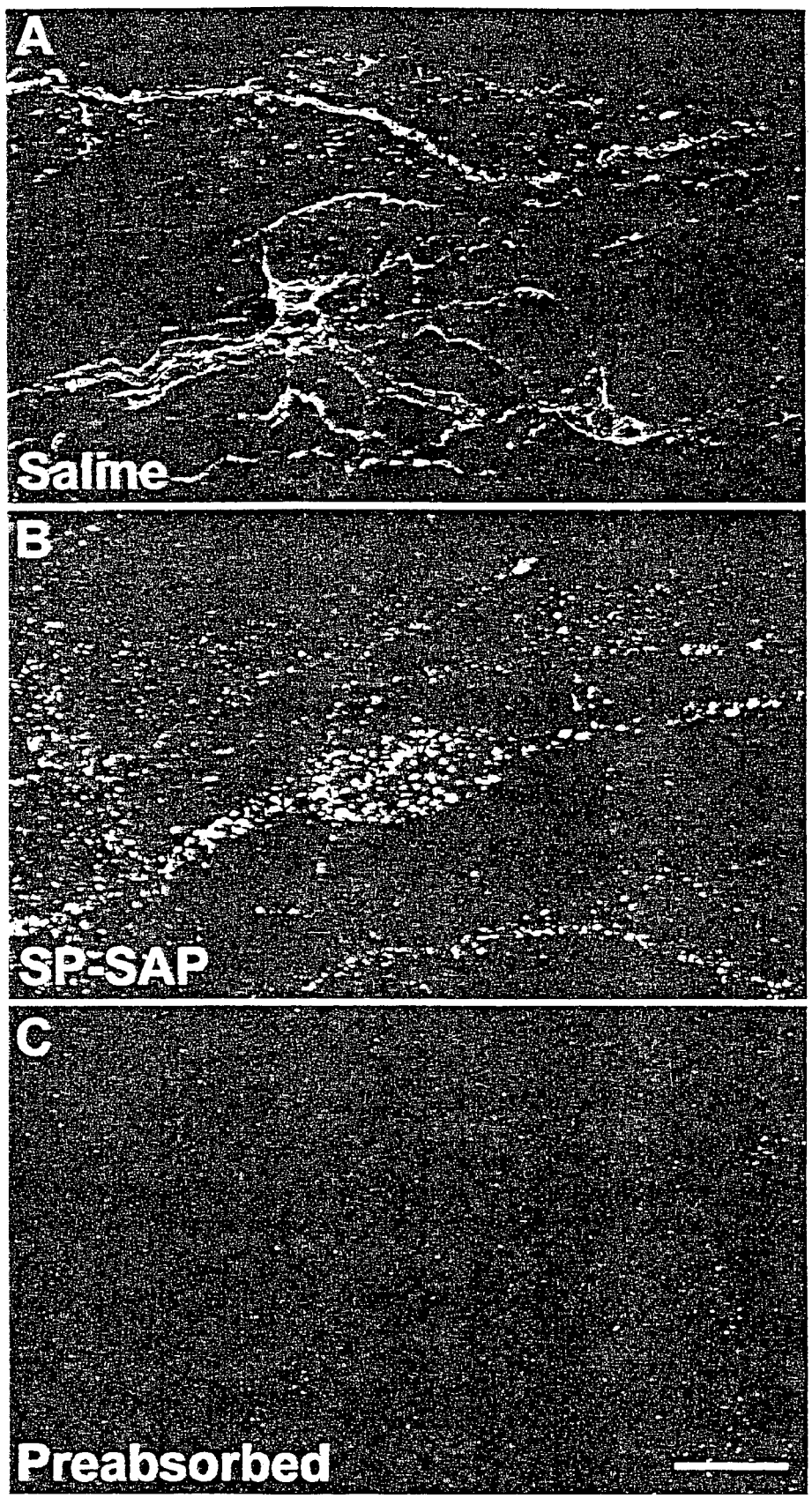
FIG. 9A-C: NK-1R-immunofluorescence in lamina I neurons of the spinal cord following SP-SAP treatment.
Figure 10:
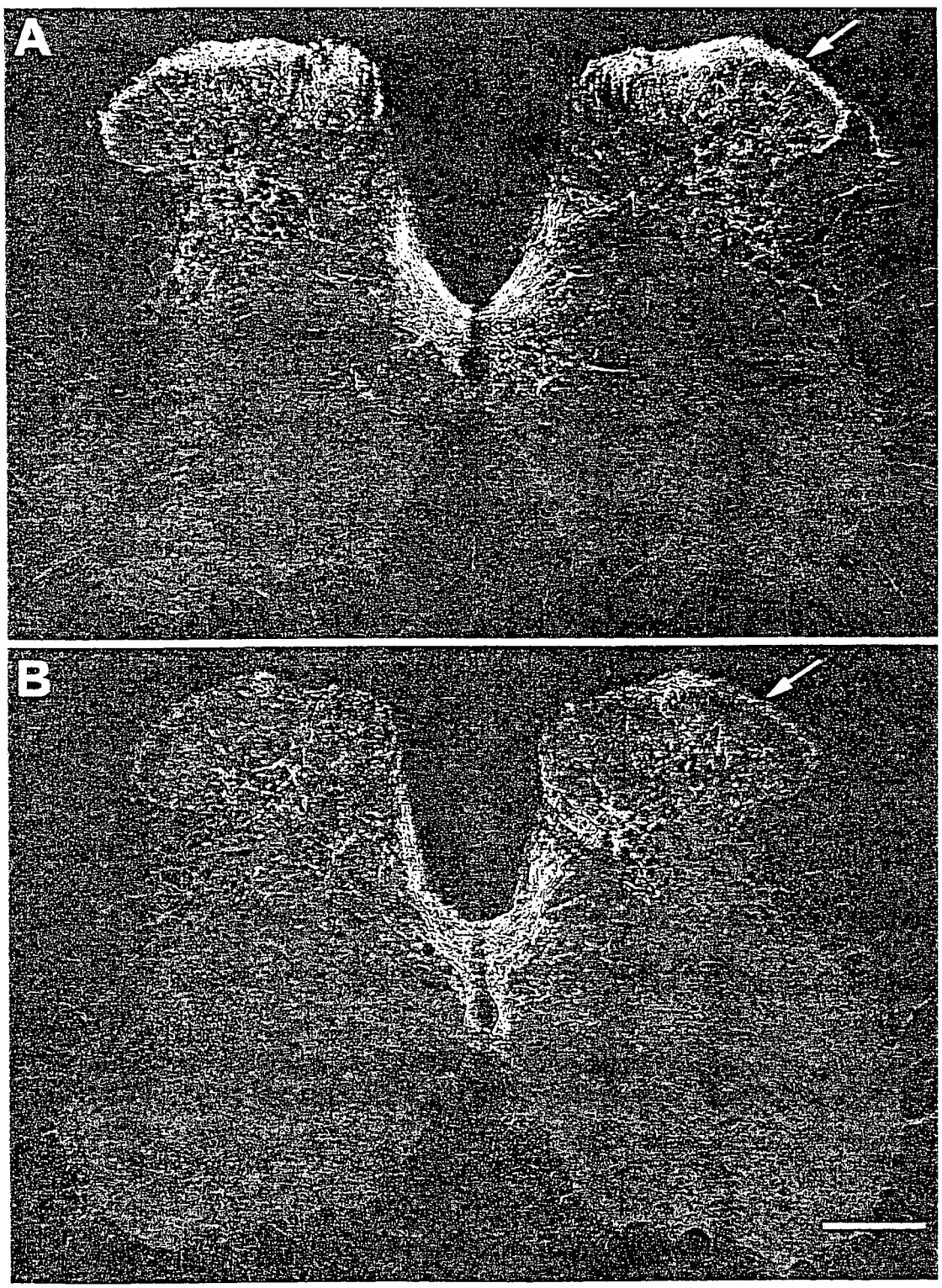
FIG. 10A-B: Cytotoxicity following intrathecal infusion of SP-SAP in the spinal cord.

To estimate the placement of the intrathecal catheter and the potential spread of SP-SAP, 10 μl of the dye Fast Green was injected with the end of the intrathecal catheter placed at L4 and, 1 hour later, the dye had intensely labeled the spinal cord from spinal segments L2-L5. Animals were anesthetized with an intramuscular injection of Ketamine (100 mg/kg) & Acepromazine (1 mg/kg) and placed in a stereotaxic frame. An 8.5-cm length of PE-10 tubing (inner diameter: 0.28 mm, outer diameter: 0.61 mm), serving as an inflow cannula, was inserted into the subarachnoid space via an incision in the atlanto-occipital membrane. The cannula terminated in the caudal region of the lumbar enlargement (approximately L4). The spinal cord was superfused with 10 μp of either saline or $5.0 \times 10^{-6}$ M SP, SAP or SP-SAP followed by a 5 μl saline flush using a 25 μl Hamilton syringe. 5 min after spinal superfusion, the cannula was carefully withdrawn and the wound closed with 3-0 silk sutures. One hour following injection of 10 μl of $5.0 \times 10^{-6}$ M SP-SAP, NK-1R internalization was observed in NK-1R-immunoreactive dendrites and cell bodies in lamina I of the spinal cord at spinal segments L2-L5 (FIG. 9). Internalization of NK-1R presumably reflected the sites where SP-SAP had bound to NK-1R and induced the internalization of both NK-1R and SP-SAP (2,39-42). Following injection of SP-SAP, a significant loss of NK-1R immunoreactivity was first detected at 7 days after treatment. This loss of NK-1R immunoreactivity was confined to lamina I in spinal segments L2-L5 and the loss of NK-1R immunofluorescence in lamina I was observed through 28 days post-treatment (FIG. 10B), which was the last time point examined. In contrast, injection of saline, SP or SAP alone produced no change in NK-1R immunoreactivity in lamina I in spinal segments L2-L5 at any of the time points examined (FIG. 10A).

Twenty-eight days following injection of saline, SP, SAP, or SP-SAP, spinal cords and dorsal root ganglia (L4) were histologically examined to determine which cell populations had been affected by these treatments (Table 2). Immunohistochemistry and fluorescent confocal microscopy was performed as previously described (46) using an MRC-1024 Confocal Imaging System (Bio-Rad, Boston, Mass.) and an Olympus BH-2 microscope equipped for epifluorescence (Lake Success, N.Y.). For cell counts the spinal cords were cut in the sagittal plane whereas for immunofluorescence measurements the spinal cords were cut in either the sagittal or coronal plane. Both of the microscopes were set up as previously described (46,47). SPR was detected by a polyclonal rabbit anti-SPR antibody (1:5000; a kind gift from S. Vigna) raised against a 15 amino acid peptide sequence ($SPR_{393-407}$) at the COOH-terminus of the rat SPR. SP was detected by a polyclonal guinea pig anti-SP antibody (1:1000, a kind gift from J. Maggio). Calbindin was detected by a monoclonal mouse anti-calbindin antibody (Sigma, 1:300). Microtubule-associated protein (MAP-2) was detected by a monoclonal mouse anti MAP-2 antibody (Sigma, 1:750). Choline acetyl transferase (CHAT) was detected by a monoclonal mouse anti-ChAT antibody (Chemicon, 1:500). Glial Fibrillary Acidic Protein was detected by a polyclonal rabbit anti-GFAP antibody (DAKO, 1:450). OX-42 was detected using a monoclonal mouse antibody (Chemicon, 1:2,000). Saporin was detected by a polyclonal goat anti-Saporin antibody (Advanced Targeting Systems, 1:350). Secondary antibodies conjugated to fluorescent markers Cy3 (used with SPR, Calbindin, ChAT, GFAP, OX-42 and Saporin) and FITC (used with SP and MAP-2; Jackson) were used at 1:600 and 1:150, respectively. All primary (overnight, 22° C.) and secondary (3 hours, 22° C.) antibodies were applied in cocktails with 1% goat serum and 0.3% Triton X-100 in PBS solution. Finally, the tissue sections were washed for 20 min in PBS (pH 7.4, 22_C), mounted onto gelatin-coated slides, and coverslipped using PBS-glycerine containing 1.0% p-phenylenediamine to reduce photobleaching.

To determine the number of immunofluorescent cell bodies (Table 1) the slides were viewed through a 1.0 cm² eyepiece grid, which was divided into one hundred 1 mm×1 mm units, and the total number of immunofluorescent cell bodies/unit area were counted. To calculate SPR immunofluorescence intensity, images of the 60 μm thick tissue sections were obtained with the BioRad MRC1024 laser scanning confocal fluorescent imaging system and analyzed using NIH Image 1.7.

Measurements were made of neuronal cell populations expressing the NK-1R (labels lamina I, III-V, and the preganglionic sympathetic neurons at spinal segment T10), calbindin (labels a subset of lamina I & II neurons), ChAT (labels motor neurons), substance P (labels cell bodies in the L4 dorsal root ganglia) as well as immunofluorescence for SP in lamina I (labels SP primary afferent inputs), MAP-2 (labels all neurons in lamina I), glial fibrillary acidic protein (labels astrocytes in laminae I) and OX-42 (labels microglia in lamina I)

Table 2 Cytotoxicity of intrathecally infused saline, SP, SAP and SP-SAP in the L4 segment of the spinal cord at 28 days post-treatment. Cell numbers and immunofluorescence levels were determined using confocal microscopy. In all cases the saline, SP and SAP animals were not significantly different from normal untreated control animals and thus, we have listed only the values for the saline, SAP and SP-SAP infused animals. The only significant difference in the SP, SAP or SP-SAP treated animals vs. saline treated controls was the loss of lamina I SPR-immunoreactive neurons and the loss of SPR-immunoreactivity in lamina I of the spinal cord in the SP-SAP treated animals. All data points represent an n=6 and are expressed as +/−s.e.m. and significant differences calculated by a one-way ANOVA and Bonferroni comparisons (* denotes P<0.01).

| Treatment (neuronal cell population) | saline | SAP | SP-SAP |
|---|---|---|---|
| | Percent immunoreactive positive cells (saline = 100) | | |
| SPR (laminae I and II) | 100 ± 27 | 80 ± 16 | 15 ± 13* |
| SPR (lamina III and IV) | 100 12 | 79 ± 13 | 86 ± 13 |
| SP (DRG) | 100 ± 23 | 91 ± 11 | 103 ± 13 |
| Calbindin (laminae I and II) | 100 ± 10 | 96 ± 7 | 93 ± 9 |
| ChAT (motor neurons) | 100 ± 16 | 116 ± 24 | 107 ± 11 |
| | Percent immunofluorescence level cells | | |
| SPR (laminae I and II) | 100 ± 9 | 95 ± 3 | 65 ± 8* |
| SPR (preganglionic sympathetic) | 100 ± 14 | 100 ± 9 | 92 ± 7 |
| SP (laminae I and II) | 100 ± 24 | 96 ± 3 | 97 ± 13 |
| GFAP (lamina I) | 100 ± 11 | 90 ± 13 | 116 ± 7 |
| MAP-2 (lamina I) | 100 ± 12 | 100 ± 14 | 100 ± 17 |

*Statistical significance from control (P < 0.05).

Examination of neuronal markers and immunofluorescence intensity values showed that the only significant changes observed at 28 days post-treatment with saline, SP, SAP, or SP-SAP was that SP-SAP treatment reduced the number of lamina I NK-1R-immunoreactive neurons in lamina I and in the levels of NK-1R immunofluorescence in lamina I (FIG. 10 & Table 2) Infusion of SP-SAP produced an 85% reduction in the number of NK-1R-immunofluorescent neurons in lamina I at spinal cord segment L4. The surviving 15% of the lamina I-immunoreactive neurons showed shrunken cell bodies, shortened cell processes and NK-1R immunoreactivity that was diffusely distributed throughout the cytoplasm with little NK-1R present on the plasma membrane. In contrast, there was not a significant reduction in the total number, or evidence or cytotoxicity, in NK-1R-immunoreactive neurons located in lamina III-V or X at the L4 spinal segment or in preganglionic sympathetic neurons at spinal segment T10 (Table 2).

Examination of the spinal cords treated with saline, SP, or SAP alone showed that these treatments did not produce a significant change in cell number, morphology or fluorescence level of any of the cell markers examined (Table 2). Thus, the cytotoxicity of intrathecally-infused SP-SAP was limited to the NK-1R-expressing lamina I neurons in spinal segments L2-L5.

Intrathecal infusion of saline, SP, SAP, or SP-SAP produced no detectable changes in body weight, food intake, alertness, locomotion or grooming behavior for 28 days after injection. Behavioral testing indicated that all animals had normal withdrawal latencies to heat applied to the plantar surface of the hindpaw prior to treatment with capsaicin. Measures of nocifensive behavior and hyperalgesia produced by intraplantar injection of capsaicin were obtained as described previously (48). Hyperalgesia is defined as an increase in withdrawal responses. The capsaicin model of hyperalgesia used in these experiments was chosen as it has been well characterized, it clearly produces hyperalgesia in humans and it is the only model of hyperalgesia that can be used in parallel animal and human studies. Capsaicin (Sigma Chemical Co., St. Louis, Mo.) was dissolved in a vehicle of 7.5% polyxyethylene sorbitan monooleate (Tween-80) and saline, and given into the plantar surface of one hindpaw. Each animal received one injection of 10 g in a volume of 10 l. The duration of nocifensive behavior, defined as lifting and guarding the injected paw, was measured for the first five minutes after injection.

Withdrawal responses to heat were determined using a procedure previously described (49). Rats were placed under a non-binding cage on a 3-mm thick glass plate which was elevated to allow maneuvering of a radiant heat source from below. Controlled radiant heat stimuli were applied to the plantar surface of the hindpaw using a 50-watt light bulb placed in a custom built case. The start of each trial activated a timer and withdrawal latencies to the nearest 0.1 sec were measured automatically by a photocell which terminated each trial and stopped the timer upon withdrawal of the paw. Four stimuli, spaced at least 1 min apart, were applied to each hindpaw. Withdrawal latency for each paw was defined as the mean latency of the last three trials. The intensity of the heat was adjusted and maintained to produce withdrawal latencies of approximately 12 seconds under normal conditions. Heat hyperalgesia was defined functionally as a decrease in the withdrawal latency.

To measure withdrawal responses to mechanical stimuli, rats were placed under a clear plastic cage on an elevated plastic mesh floor (1 $cm^2$ perforations). A von Frey monofilament with a bending force of 95.0 mN was applied to the planter surface from below the floor. The stimulus was applied 10 times, each for a duration of 1-2 seconds, at random locations on the plantar surface. The frequency was determined for each hindpaw. Mechanical hyperalgesia was defined as an increase in withdrawal response frequency.

Figure 11:
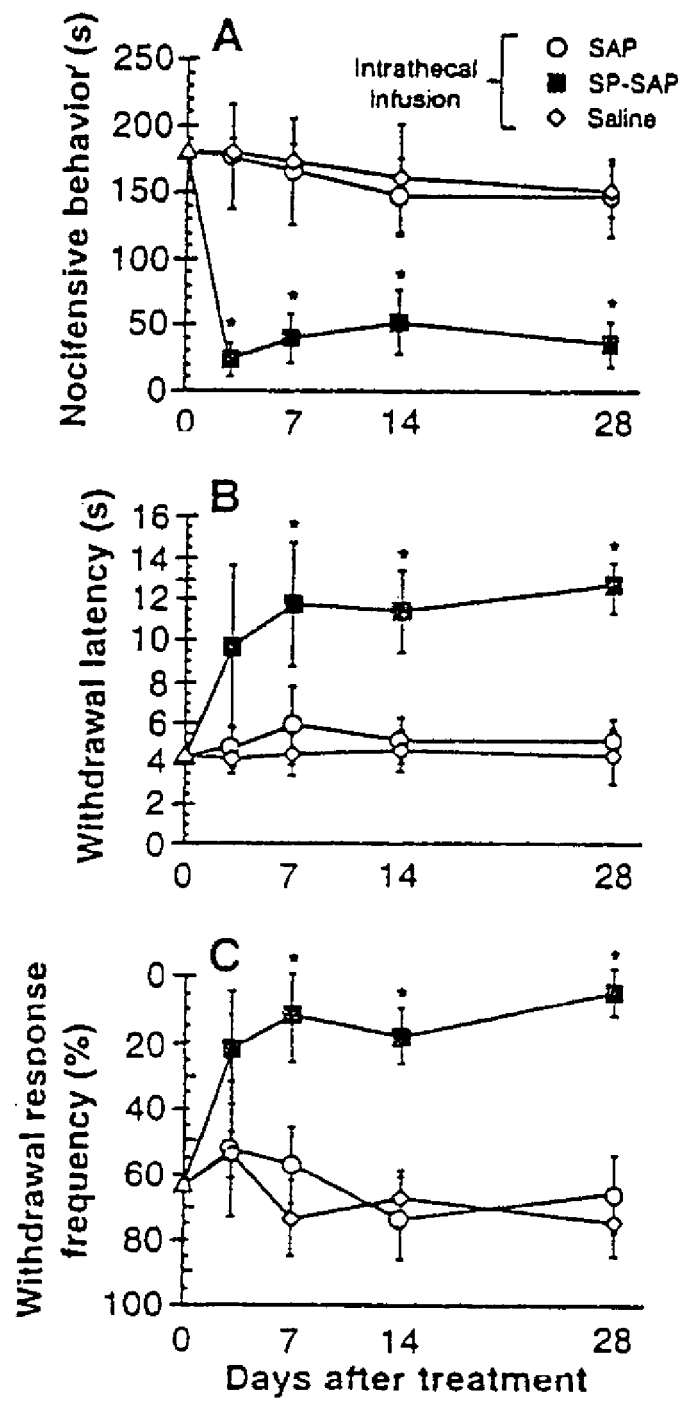
FIG. 11A-C: Three behavioral parameters following intrathecal infusion of saline, SAP or SP-SAP at day 0.

In untreated rats, intraplantar injection of 10 g of capsaicin produced nocifensive behavior for a duration of approximately 3 min and produced approximately a 50% decrease in withdrawal latency to heat and a 40-60% increase in the frequency of withdrawal from the mechanical stimuli (48,50). Animals pretreated with SP-SAP exhibited a significant attenuation of mechanical (85% decrease at day 28) and heat (60% decrease at day 28) hyperalgesia produced by intraplantar injection of capsaicin (FIG. 11). Additionally, there was a profound reduction (75% decrease at day 28) in the nocifensive behavior induced by unilateral injection of capsaicin into the hindpaw at days 7, 14, and 28 after intrathecal pretreatment (FIG. 11). In contrast, infusion of saline, SP, or SAP produced no significant change in mechanical or thermal hyperalgesia, or in nocifensive behavior produced by capsaicin when compared to normal untreated animals in any corresponding time point examined (FIG. 11).

Although we ablated only the NK-1R-expressing neurons, which constitute less than 10% of all lamina I neurons (2,40), capsaicin-induced nocifensive behavior and mechanical and thermal hyperalgesia were depressed by 60-90% (FIG. 11). Our assumption is that intrathecal infusion of SP-SAP is more cytotoxic to NK-1R-expressing lamina I cells than NK-1R-expressing cells in laminae III-V because further spread of bioactive SP-SAP into deeper laminae was prevented by degradation of the SP moiety by characterized proteases. One reason that ablation of such a small percentage of lamina I neurons could produce such a large change in behavioral nociceptive responses may be that, as the majority of lamina I spinothalamic and spinoparabrachial neurons express NK-1R (43,44) and internalize SP-SAP, SP-SAP treatment is ablating a major part of the system for the ascending conduction of nociceptive information.

It has been demonstrated that hyperalgesia produced by capsaicin is mediated in part by sensitization of spinothalamic neurons and that SP is involved in the excitation and sensitization of spinothalamic neurons (51-53) and the development of hyperalgesia (54-57). However, it has been surprisingly difficult to block noxious stimulus-evoked pain behavior with either SP antagonists (58-60) or "knock-out" of NK-1R in mice (61). In the present study we have not blocked or inactivated only NK-1R, but rather we have killed a specific population of NK-1R-expressing cells that also express a variety of other neurotransmitter receptors (61). These data suggest that while this small population of NK-1R-expressing neurons is pivotal in the maintenance of hyperalgesia, a variety of other non-NK-1R expressed by these neurons are also involved in nociceptive signaling and that elimination of these neurons can eliminate the transmission of chronic pain.

Further experiments have shown that the elimination of the NK-1R+ neurons eliminates chronic pain in other models of both inflammatory and neuropathic pain. In one of these models, the chronic pain was established previous to treatment with SP-SAP. In this model (62), tight ligation of the rat L5 and L6 spinal nerves result in a long-lasting mechanical allodynia that is present 7 days post-ligation. After SP-SAP treatment, the chronic pain transmission was inhibited. In addition, 200 days after the treatment with SP-SAP, the effect of inhibition of chronic pain transmission is still present, with no formation of a central pain state that can appear after spinal cord surgical intervention, a common treatment of chronic pain (63).

Chronic, neuropathic pain: Although the mechanism(s) by which nerve injuries produce chronic pain is not entirely clear, several hypotheses have involved a central role for substance P. Certainly, clinical manamgement and patient responses to treatment of chronic neurophathic pain are very difference from acute pain. The models we propose to study involve sciatic nerve transection in midthigh similar to our previous studies of sensory plasticity and sciatic nerve ligation in midthigh. In rats with sciatic transections, suppression of automony will be taken to indicate decreased pain. Although there is some dispute about the precise relationship of autotomy to human experience, the current consensus is that it does relate to such clinical problems as phantom limb pain. SP also has been implicated in the development of mechanical allodynia seen with sciatic ligatures. This may reflect the hyperpathia seen in some patients with neuropathic pain.

The findings of this experiment are of great importance to any possible therapeutic use of SSP-SAP in patients who have neurophathic pain, a common clinical situation. Our hypothesis is that destruction of lamina I NK-1R+ neurons will diminish autotomy by preventing rostral propagation of inapproriate neural activity.

The formalin test has made important contributions to the battery of tests used in basic pain research. It is considered to be one of the standard animal models of nociception that occurs in humans.

In conclusion, results here indicate that SP-SAP and [Sar$^9$, Met $(0_2)^{11}$]—SP-SAP are important agents in the control of chronic pain. This could have a great impact on the many types of chronic pain that are now untreatable or intractable.

REFERENCES

1. Nakaya Y, Kaneko T, Shigemoto R, Nakanishi S, Mizuno N. 1994. Immunohistochemical localization of substance P receptor in the central nervous system of the adult rat. J. Comp. Neurol. 347:249-274.
2. Brown J L, Liu H, Maggio J E, Vigna S R, Mantyh P W, Basbaum A I. 1995. (Morphological characterization of substance P receptor-immunoreactive neurons in the rat spinal cord and trigeminal nucleus caudalis. J. Comp. Neurol. 356:327-344.
3. Picard P, Regoli D, Couture R. 1994. Cardiovascular and behavioural effects of centrally administered tachykinins in the art: characterization of receptors with selective antagonists. Br. J. Pharmacol. 112:240-249.
4. Humpel C, Saria A. 1993. Intranigral injection of selective neurokinin-1 and neurokinin-3 but not neurokinin-2 receptor agonists biphasically modulate striatal dopamine metabolism but not striatal preprotachykinin-A mRNA in the rat. Neurosci. Lett. 157:223-226.
5. Guzman R G, Kendrick K M, Emson P C. 1993. Effect of substance P on acetylcholine and dopamine release in the rat striatum: a microdialysis study. Brain Research 622: 147-154.
6. Anderson J J, Kuo S, Chase T N, Engber T M. 1994. Dopamine $D_1$ receptor-stimulated release of acetycholine in rat striatum is mediated indirectly by activation of striatal neurokinin$_1$ receptors. J. Pharmacol. Exp. Therap. 269: 1144-1151.
7. Yashpal K, Pitcher G M, Henry J I. 1995. Noxious peripheral stimulation produces antinociception mediated via substance P and opioid mechanisms in the rat tail-flick test. Brain Res. 674:97-103.
8. Neugebauer V, Schaible H G, Weiretter F. Freudenberger U. 1994. The involvement of substance P and neurokinin-1 receptors in the responses of rat dorsal horn neurons to noxious but not to innocuous mechanical stimuli applied to the knee koint. Brain Res. 666:207-215.
9. Chapman V, Dickenson A H. 1993. The effect of intrathecal administration of RP67580, a potent neurokinin 1 anatagonist on nociceptive transmission in the rat spinal cord. Neurosci. Lett. 157:149-152.
10. McCarson K E, Krause J E. 1995. The formalin-induced expression of tachkinin peptide and neurokinin receptor message RNAs in rat sensory ganglia and spinal cord is mediated by opiate preadministration. Neuroscience 64:729-739.
11. Luo L, Wiesenfeld-Hallim Z. 1995. The effects of pre-treatment with tachykinin antagonists and galanin on the development of spinal cord hyperexcitability following sciatic nerve section in the rat. Neuropeptides 28:161-166.
12. Yashpal K, Kar S, Quirion R, Hui-Chan C W, Henry J I. 1995. Noxious stimulation decreases substance P binding in rat spinal dorsal horn: competition by endogenous ligand? NeuroReport 5:2101-2104.
13. Sann H, Jansco G, Rossler W, Pierau F K. 1995. Reduction of substance P binding sites in the spinal dorsal horn after perineural capsaicin treatment in the rat. Neurosci. Lett. 190:151-154.
14. Kar S, Rees R G, Quirion R. 1994. Altered calcitonin gene-related peptide, substance P and enkephalin immunoreactivities and receptor binding sites in the dorsal spinal cord of the polyarthritic rat. Eur. J. Neurosci. 6:345-354.
15. Smith C, Harrison S, Bowers J, Wiseman J, Birch P. 1994. Non-specific effects of the tachykinin NK1 receptor antagonist, CP-99,994, in antinociceptive tests in rat, mouse and gerbil. Eur. J. Pharmacol. 271:481-487.
16. Neugebauer V, Weiretter F, Schaible H G. 1995. Involvement of substance P receptors in the hyperexcitability of dorsal horn neurons during the development of acute arthritis in rat's knee joint. J. Neurophysiol. 73:1574-1583.
17. Tadano T, Asao T, Aizawa T, Sakurada S, Abe Y, Yonezawa A, Ando R, Arai Y, Kinemuchi H, Kisara K. 1995. Immunohistochemical determination of rat spinal cord substance P, and antinociceptive effect during development of thiamine deficiency. Brain Res. 696:21-29.
18. Stirpe F, Casper-Campani A, Barbieri L, Falasca A, Abbondanza A, Stevens W A. 1983. Ribosome-inactivating proteins from the seeds of *Saponaria officinalis* L. (soapwort) of *Agrostemma githago* L. (corn cockle) and of *Asparagus officinalis* (asparagus) and from the latex of *Hura crepitans* L. (sandbox tree). Biochem. J. 216:617-625.
19. Anton P A, Reeve Jr, J. R., Vidrich A, Mayer E, Shanahan S. 1991. Development of a biotinylated analog of substance P for use as a receptor probe. Laboratory Investigation 64:703-708.
20. Lambert J M, Senter P D, Yau-Young A, Blattler W A, Goldmacher V S. 1985. Purified immunotoxins that are reactive with human lymphtoid cells. J. Biol. Chem. 260: 12035-12041.
21. Lappi D A, Matsunami R, Martineau D, Baird A. 1993. Reducing the heterogeneity of chemically conjugated targeted toxins: homogeneous basic FGF-saporin. Analytical Biochemistry 212:446-451.
22. Lappi D A, Martineau D, Sarmientos P, Garofano L, Aranda A P, Miyajima A, Kitamura T, Baird A. 1993. Characterization of a saporin mitotoxin specifically cytotoxic to cells bearing the granulocyte-macrophage colony-stimulating factor. Growth Factors 9:31-39.
23. Lappi D A, Esch F S, Barbieri L, Stirpe F, Soria M. 1985. Characterization of a *Saponaria officinalis* seed ribosome-inactivating protein: immunoreactivity and sequence homologies. Biochem. Biophys. Res. Commun. 129:934-942.

24. Lappi D A, Martineau D, Baird A. 1989. Biological and chemical characterization o basic FGF-saporin mitotoxin. Biochem. Biophys. Res. Commun. 160:917-923.

25. Buechler Y J, Sosnowski B A, Victor B A, Parandoosh Z, Bussell S J, Shen C, Ryder M, Houston L L. 1995. Synthesis and characterization of a homogeneous chemical conjugate between basic fibroblast growth factor and saporin. Eur. J. Biochem. 234:706-713.

26. Mantyh P W, Allen C J, Rogers S D, DeMaster E, Ghilardi J R, Mosconi T, Kruger L, Mannon P J, Taylor I L, Vigna S R. 1994. Some sensory neurons express neuropeptide Y receptors: potential paracrine inhibition of primary afferent nociceptors following peripheral nerve injury. J. Neurosci. 14:3958-3968.

27. Vigna S R, Bowden J J, McDonald D M, Fisher J, Okamoto A, McVey D C, Payan D G, Bunnett N W. 1994. Characterization of antibodies to the rat substance P (NK-1) receptor and to a chimeric substance P receptor expressed in mammalian cells. J. Neurosci. 14:834-845.

28. Grady E F, Garland A M, Gamp P D, Lovett M, Payan D G, Bunnett N W. 1995. Delineation of the endocytotic pathway of substance P and its seven-transmembrane domain NK1 receptor. Mol. Biol. Cell 6:509-524.

29. Hokfelt T, Kellerth J O, Nilsson G, Pernow B. 1975. Experimental immunohistochemical studies on the localization and distribution of substance P in cat primary sensory neurons. Brain Research 100:235-252.

30. Boehmer C G, Norman J, Catton M, Fine L G, Mantyh P W. 1989. High levels of mRNA coding for substance P, somatostatin and alpha-tubulin are expressed by rat and rabbit dorsal root ganglia neurons. Peptides 10:1179-1194.

31. Quartu M, Diaz G, Floris A, Lai M L, Priestley J V, Del Fiacco M. 1992. Calcitonin gene-related peptide in the human trigeminal sensory system at developmental and adult life stages: immunohistochemistry, neuronal morphometry and coexistence with substance P. J. Chem. Neuroanat. 5:143-157.

32. Del Fiacco M, Quartu M, Priestley J V, Setzu M D, Lai M L. 1994. GAP-43 persists in adulthood and coexists with SP and CGRP in human trigeminal sensory neurones. NeuroReport 5:2349-2352.

33. Brimijoin S, Lundberg J M, Brodin E, Hokfelt T, Nilsson G. 1980. Axonal transport of substance P in the vagus and sciatic nerves of the guinea pig. Brain Research 191:443-457.

34. Jessell T M, Iversen L L. 1977. Opiate analgesics inhibit substance P release from rat trigeminal nucleus. Nature 268:549-551.

35. Schaible H G, Jarrott B, Hope P J, Duggan A W. 1990. Release of immunoreactive substance P in the spinal cord during development of acute arthritis in the knee joint of the cat: a study with antibody microprobes. Brain Research 529:214-223.

36. Duggan A W, Hope P J, Lang C W, Williams C A. 1991. Sustained isometric contraction of skeletal muscle results in release of immunoreactive neurokinins in the spinal cord of the anaesthetized cat. Neurosci. Lett. 122:191-194.

37. Salter M W, Henry J I. 1991. Responses of functionally identified neurones in the dorsal horn of the cat spinal cord to substance P, neurokinin A and physalaemin. Neuroscience 43:601-610.

38. De Koninck Y, Henry J I. 1991. Substance P-mediated slow excitatory postsynaptic potential elicited in dorsal horn neurons in vivo by noxious stimulation. Proc. Natl. Acad. Sci. USA 88:11344-11348.

39. Liu H. Brown J L, Jasmin L, Maggio J E, Vigna S R, Mantyh P W. 1994. Synaptic relationship between substance P and the substance P receptor: light and electron microscopic characterization of the mismatch between neuropeptides and their receptors. Proc. Natl. Acad. Sci. USA 91:1009-1013.

40. Littlewood N K, Todd A J, Spike R C, Watt C, Shehab S A. 1995. The types of neuron in spinal dorsal horn which possess neurokinin-1 receptors. Neuroscience 66:597-608.

41. Mantyh P W, DeMaster E, Malhotra A, Ghilardi J R, Rogers S D, Mantyh C R, Liu H, Basbaum A I, Vigna S R, Maggio J E, Simone D A. 1995. Receptor endocytosis and dendrite reshaping in spinal neurons after somatosensory stimulation. Science 268:1629-1632.

42. Abbadie C, Trafton J, Liu H, Mantyh P W, Basbaum A I. 1997. Inflammation increases the distribution of dorsal horn neurons that internalize the neurokinin-1 receptor in response to noxious and non-noxious stimulation. J. Neurosci. 17:8049-8060.

43. Ding Y Q, Takada M, Shigemoto R, Mizumo N. 1995. Spinoparabrachial tract neurons showing substance P receptor-like immunoreactivity in the lumbar spinal cord of the rat. Brain Research 674:336-340.

44. Marshall G E, Shehab S A, Spike R C, Todd A J. 1996. Neurokinin-1 receptors on lumbar spinothalamic neurons in the rat. Neuroscience 72:255-263.

45. Stirpe F. Barbieri L, Battelli N C, Soria M, Lappi D A. 1992. Ribosome-inactivating proteins from plants: present status and future prospects. Bio/Technology 10:405-412.

46. Brelje T C, Scharp D W, Sorenson R L. 1989. Three-dimensional imaging of intact isolated islets of Langerhans with confocal microscopy. Diabetes 38:808-814.

47. Mantyh P W, Rogers S D, Allen C J, Catton M D, Ghilardi J R, Levin L A, Maggio J E, Vigna S R. 1995. Beta 2-adrenergic receptors are expressed by glia in vivo in the normal and injured central nervous system in the rat, rabbit, and human. J. Neurosci. 15:152-164.

48. Gilchrist H D, Allard B L, Simone D A. 1996. Enhanced withdrawal responses to heat and mechanical stimuli following intraplantar injection of capsaicin in rats. Pain 67:179-188.

49. Hargreaves K, Dubner R, Brown F, Flores C, Joris J. 1988. A new and sensitive method for measuring thermal nociception in cutaneous hyperalgesia. Pain 32:77-88.

50. Simone D A. 1992. Neural mechanisms of hyperalgesia. Curr. Opin. Neurobiol. 2:479-483.

51. Dougherty P M, Willis W D. 1991. Enhancement of spinothalamic neuron responses to chemical and mechanical stimuli following combined micro-iontophoretic application of N-methyl-D-aspartic acid and substance P. Pain 47:85-93.

52. Simone D A, Sorkin L S, Oh U, Chung J M, Owens C, LaMotte R H, Willis W D. 1991. Neurogenic hyperalgesia: central neural correlates in responses of spinothalamic tract neurons. J. Neurophysiol. 66:228-246.

53. Dougherty P M, Palecek J, Zorn S. Willis W D. 1993. Combined application of excitatory amino acids and substance P produces long-lasting chances in responses of primate spinothalamic tract neurons. Brain Res. Brain Res. Rev. 18:227-246.

54. Malmberg A B, Yaksh T L. 1992. Hyperalgesia mediated by spinal glutamate or substance P receptor blocked by spinal cyclooxygenase inhibition. Science 257:1276-1279.

55. Nagy I, Miller B A, Woolf C J. 1994. NK1 and NK2 receptors contribute to C-fibre evoked slow potentials in the spinal cord. NeuroReport 5:2105-2108.

56. Ma Q P, Woolf C J. 1995. Involvement of neurokinin receptors in the induction but not the maintenance of 56. mechanical allodynia in rat flexor motoneurones. J. Physiol. (London) 486:769-777.
57. Traub R J. 1996. The spinal contribution of substance P to the generation and maintenance of inflammatory hyperalgesia in the rat. Pain 67:151-161.
58. Munro F E, Fleetwood-Walker S M, Parker R M, Mitchell R. 1993. The effects of neurokinin receptor antagonists on mustard oil-evoked activation of rat dorsal horn neurons. Neuropeptides 25:299-305.
59. Nagy I, Maggi C A, Dray A, Woolf C J, Urban L. 1993. The role of neurokinin and N-methyl-D-aspartate receptors in synaptic transmission from capsaicin-sensitive primary afferents in the rat spinal cord in vitro. Neuroscience 52:1029-1037.
60. Nagy I, Maggi C A, Dray A, Woolf C J, Urban L. 1993. The role of neurokinin and N-methyl-D-aspartate receptors in synaptic transmission from capsaicin-sensitive primary afferents in the rat spinal cord in vitro. Neuroscience 52:1029-1037.
61. Yamamoto T, Shimoyama N, Mizuguchi T. 1993. Effects of FK224, a novel cyclopeptide NK1 and NK2 antagonist, and CP-96,345, a nonpeptide NK1 antagonist, on development and maintenance of thermal hyperesthesia evoked by carrageenan injection in the rat paw. Anesthesiology 79:1042-1050
62. Bozic C R, Lu B, Hopken U E, Gerard C, Gerard N P. 1996. Neurogenic amplification of immune complex inflammation. Science 273:1722-1725.
63. Kim S H, Chung P J. 1992. An experimental model for peripheral neuropathy produced by segmental spinal nerve ligation in the rat. Pain 50:355-363.
64. Nichols M L, Allen B J, Rogers S D, Ghilardi J R, Honore P, Li J, Lappi D A, Simone D A, Mantyh P W. 1999. Transmission of chronic nociception by spinal neurons expressing the substance P receptor. Science 286:1558-1561.

What is claimed is:

1. A conjugate comprising a Substance P analog and a polypeptide that inhibits protein synthesis, wherein the analog is selected from CYGGGGGGRPKPQQFF SarLMet (O$_2$)-amide (SEQ ID NO:1) and CYGGGGGGRPKPQQFF-GLM-amide (SEQ ID NO:2).

2. The conjugate of claim 1, wherein said analog of Substance P is CYGGGGGGRPKPQQFF SarLMet (O$_2$)-amide (SEQ ID NO:1).

3. The conjugate of claim 1, wherein said analog of Substance P is CYGGGGGGRPKPQQFFGLM-amide (SEQ ID NO:2).

4. The conjugate of claim 1, wherein said polypeptide that inhibits protein synthesis is attached to said Substance P analog through a disulfide linkage.

5. The conjugate of claim 1, wherein said polypeptide that inhibits protein synthesis is saporin.

6. The conjugate of claim 1, wherein said polypeptide that inhibits protein synthesis is a ribosome-inactivating protein.

7. The conjugate of claim 6, wherein said ribosome-inactivating protein is selected from ricin A chain, gelonin and pokeweed antiviral protein.

8. The conjugate of claim 1, wherein said polypeptide that inhibits protein synthesis is a toxin.

9. The conjugate of claim 8, wherein said toxin is diphtheria toxin A fragment or an analog thereof that inhibits protein synthesis.

10. The conjugate of claim 8, wherein said toxin is pseudomonas aeruginosa exotoxin A fragment or an analog thereof that inhibits protein synthesis.

11. A pharmaceutical composition comprising a therapeutically effective amount of the conjugate of claim 1, and a pharmaceutically acceptable carrier.

12. A pharmaceutical composition comprising a therapeutically effective amount of the conjugate of claim 5, and a pharmaceutically acceptable carrier.

13. The conjugate of claim 7, wherein said ribosome-inactivation protein is ricin A chain.

14. The conjugate of claim 7, wherein said ribosome-inactivation protein is gelonin.

15. The conjugate of claim 7, wherein said ribosome-inactivation protein is pokeweed antiviral protein.

16. The conjugate of claim 1, wherein said polypeptide that inhibits protein synthesis is attached to said Substance P analog through a chemical bond.

* * * * *

SEQUENCE LISTING

```
<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: Xaa = Sar
<220> FEATURE:
<223> OTHER INFORMATION: Description of Artificial Sequence: Substance P
      analog

<400> SEQUENCE: 1

Cys Tyr Gly Gly Gly Gly Gly Gly Arg Pro Lys Pro Gln Gln Phe Phe
  1               5                  10                  15

Xaa Leu Met

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Substance P
      analog

<400> SEQUENCE: 2

Cys Tyr Gly Gly Gly Gly Gly Gly Arg Pro Lys Pro Gln Gln Phe Phe
  1               5                  10                  15

Gly Leu Met

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Substance P
      analog
<220> FEATURE:
<223> OTHER INFORMATION: Xaa = Sar

<400> SEQUENCE: 3

Cys Tyr Gly Gly Gly Gly Gly Gly Xaa Met
  1               5                  10
```

```
<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Substance P

<400> SEQUENCE: 4

Arg Pro Lys Pro Gln Gln Phe Phe Gly Leu Met
 1               5                  10

<210> SEQ ID NO 5
<211> LENGTH: 21
<212> TYPE: PRT
<213> ORGANISM: Artificial Sequence
<220> FEATURE:
<223> OTHER INFORMATION: Xaa = PyS
<220> FEATURE:
<223> OTHER INFORMATION: Description of Artificial Sequence: Substance P
      analog

<400> SEQUENCE: 5

Asn Xaa Cys Tyr Gly Gly Gly Gly Gly Arg Pro Lys Pro Gln Gln
 1               5                  10                  15

Phe Phe Gly Leu Met
            20
```